(12) United States Patent
Mukaidani et al.

(10) Patent No.: US 7,560,279 B2
(45) Date of Patent: Jul. 14, 2009

(54) METHOD OF PROLIFERATING HUMAN HEPATOCYTES AND METHOD FOR OBTAINING HUMAN HEPATOCYTES

(75) Inventors: Chise Mukaidani, Hiroshima (JP); Katsutoshi Yoshizato, Hiroshima (JP)

(73) Assignee: Hiroshima Industrial Promotion Organization, Hiroshima (JP)

( * ) Notice: Subject to any disclaimer, the term of this patent is extended or adjusted under 35 U.S.C. 154(b) by 0 days.

(21) Appl. No.: 10/509,032

(22) PCT Filed: Mar. 25, 2003

(86) PCT No.: PCT/JP03/03623

§ 371 (c)(1), (2), (4) Date: Feb. 9, 2005

(87) PCT Pub. No.: WO03/080821

PCT Pub. Date: Feb. 10, 2003

(65) Prior Publication Data

US 2005/0255591 A1 Nov. 17, 2005

(30) Foreign Application Priority Data

Mar. 25, 2002 (JP) ............................. 2002-084280

(51) Int. Cl.
*C12N 5/08* (2006.01)
*C12N 5/00* (2006.01)
*G01N 33/00* (2006.01)

(52) U.S. Cl. ............................ 435/370; 435/325; 800/3

(58) Field of Classification Search ........................ None
See application file for complete search history.

(56) References Cited

U.S. PATENT DOCUMENTS 6,509,514 B1 * 1/2003 Kneteman et al. ............... 800/3
6,825,395 B1 * 11/2004 Murakami et al. ............. 800/14

FOREIGN PATENT DOCUMENTS

| EP | 682106 | 5/1996 |
| EP | 990663 | 4/2000 |
| WO | 00/03001 | 1/2000 |
| WO | 00/43498 | 7/2000 |

OTHER PUBLICATIONS

Dandri, M et al., Hepatology 33(4):abtract, 2001.*
Ohashi, K et al. J Mol Med 79:617-630. 2001.*
Pietschmann, T and R Bartenschlager. Clin Liver Dis 7(1):23-43, 2003. abstract only.*
Turrini, P et al. Transplantation Proceedings 38:1181-1184, 2006.*
Brown, JJ et al. Hepatology 31:173-181, 2000.*
Dandri, M et al. Hepatology 33:981-988, Apr. 2001.*
Alpini, G et al. Heptology 20(2):494-514, 1994.*
Tateno, C et al. Am J Path 165(3):901-912, 2004.*
J. L. Heckej et al., "Neonatal Bleeding in Transgenic Mice Expressing Urokinase-Type Plasminogen Activator", Cell, vol. 62, pp. 447-456, Aug. 10, 1990.
J. A. Rhim et al., "Replacement of Diseased Mouse Liver by Hepatic Cell Transplantation", Science, vol. 263, pp. 1149-1152, Feb. 25, 1994.
E. P. Sandgren et al., "Complete Hepatic Regeneration after Somatic Deletion of an Albumin-Plasminogen Activator Transgene", Cell, vol. 66, pp. 245-256, Jul. 26, 1991.
J. A. Rhim et al., "Complete Reconstitution of Mouse Liver with Xenogeneic Hepatocytes", Proc. Natl. Acad., USA, vol. 92, pp. 4942-4946, May 1995.
M. Dandri et al., "Woodchuck Hepatocytes Remain Permissive for Hepadnavirus Infection and Mouse Liver Repopulation after Cryopreservation", Hepatology, vol. 34, No. 4, pp. 824-833, 2001.
M. Dandri et al., "Repopulation of Mouse Liver with Human Hepatocytes and In Vivo Infection with Hepatitis B Virus", Hepatology, vol. 33, No. 4, pp. 981-987, 2001.
J. Petersen et al., "Liver Repopulation with Xenogenic Hepatocytes in B and T Cell-Deficient Mice Leads to Chronic Hepadnavirus Infection and Clonal Growth of Hepatocellular Carcinoma", Proc. Natl. Acad. Sci., USA, vol. 95, pp. 310-315, Jan. 1998.
D. F. Mercer et al., "Hepatitis C Virus Replication in Mice with Chimeric Human Livers", Nature Medicine, vol. 7, No. 8, pp. 927-932, Aug. 2001.

* cited by examiner

*Primary Examiner*—Deborah Crouch
*Assistant Examiner*—Marcia S Noble
(74) *Attorney, Agent, or Firm*—Wenderoth, Lind & Ponack, L.L.P.

(57) ABSTRACT

Transplanting human hepatocytes into a liver of an immunodeficient hepatopathy mouse, and then feeding the mouse transplanted with the human hepatocytes under such a condition as being protected from the attack by human complement produced by the human hepatocytes thereby proliferating the transplanted human hepatocytes in the mouse liver. Further, obtaining human hepatocytes in large scale by repeating the above steps using the proliferated human hepatocytes.

6 Claims, 22 Drawing Sheets

Fig. 5
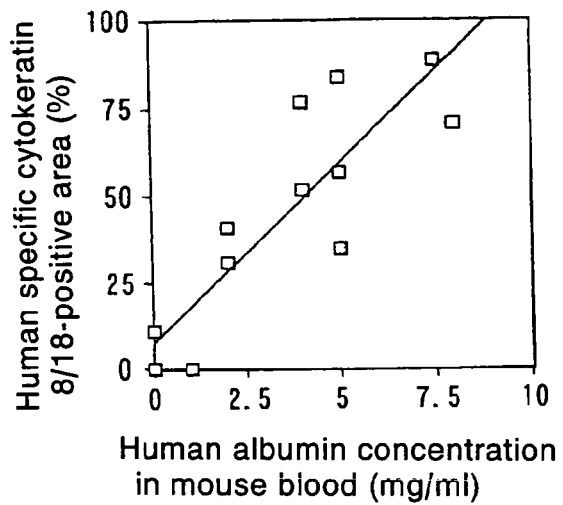
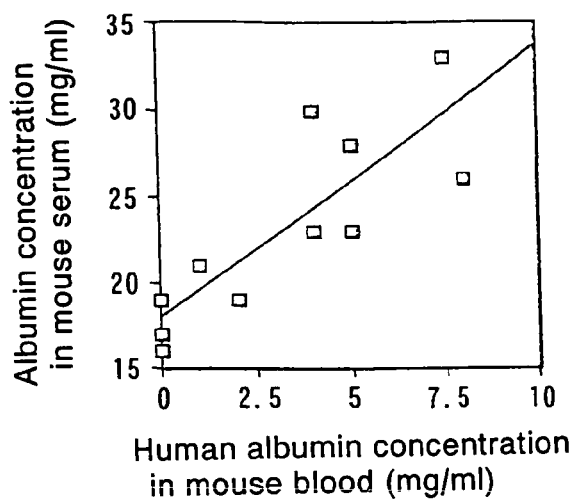
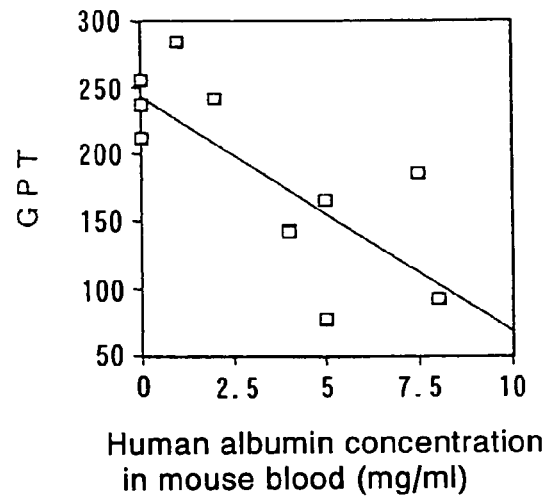

Fig. 15
Human hepatocytes (12 years old) used as an antigen to prepare a monoclonal antibody
Primary culture
At 30 days
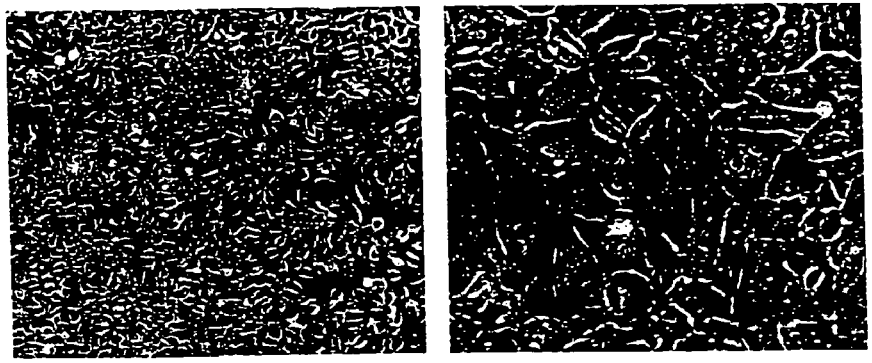
At 43 days
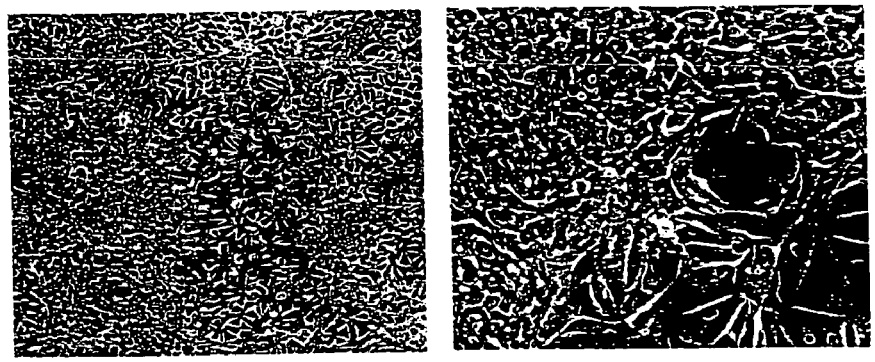
Subculture (3 passages)→immunizing mice
After 33 days
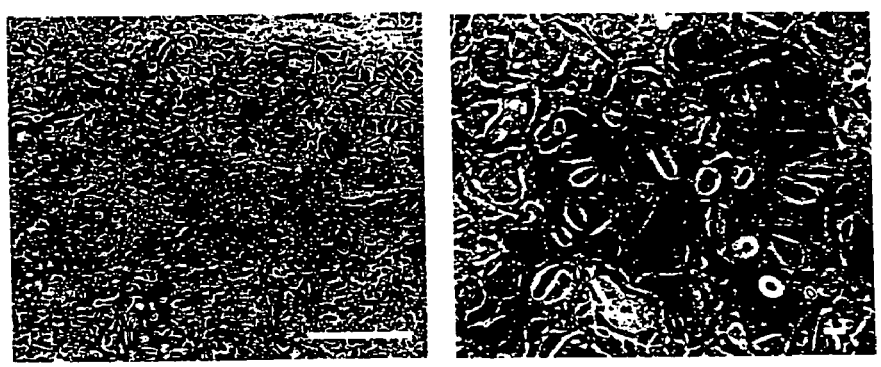
Bar, 100 μm

Fig. 16
Human tissue (62 years old)
Hybridoma culture supernatant (K8223)
K8223
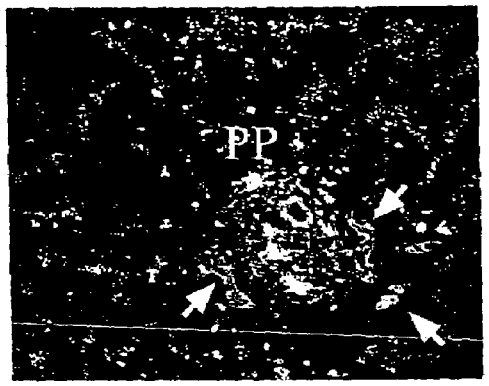
No primary antibody
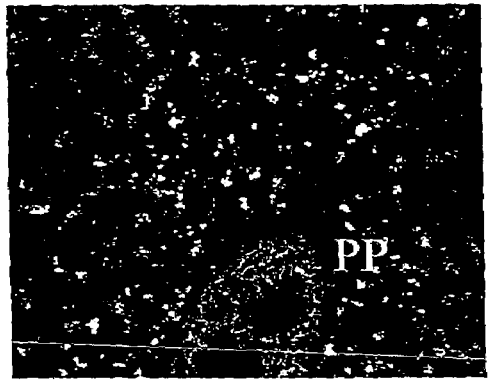
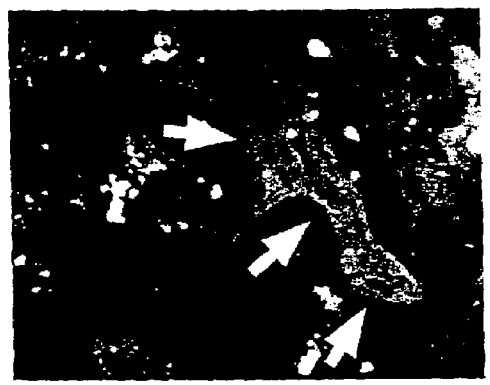
Bar, 50 μm
PP: Portal region

Fig. 18
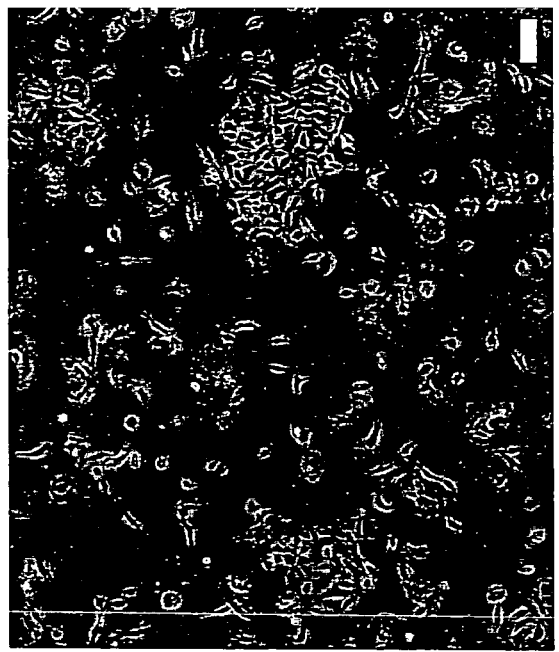
At day 8 in culture
Bar, 100 μm
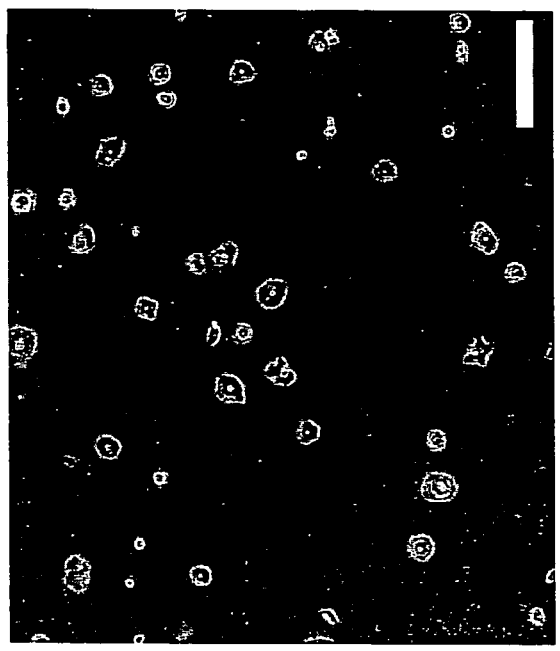
Hybridoma culture supernatant: No.23
Isolated human hepatocytes (49 yeas old)
At day 1 in culture
Before sorting

Fig. 18/1
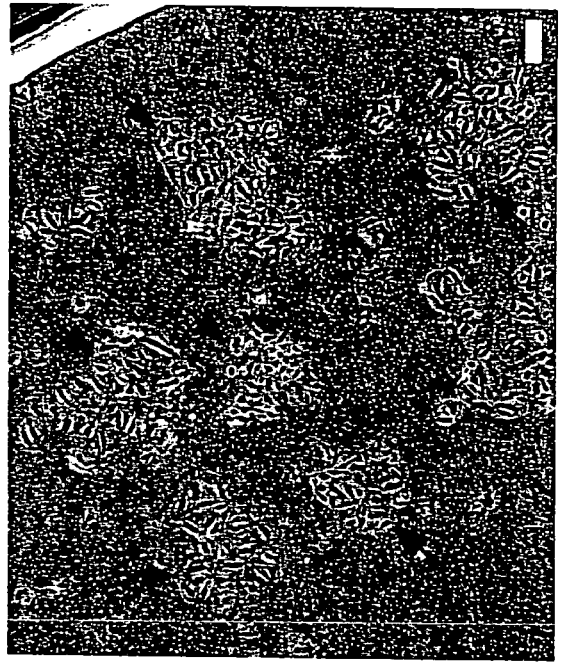
At day 8 in culture
Bar, 100 μm
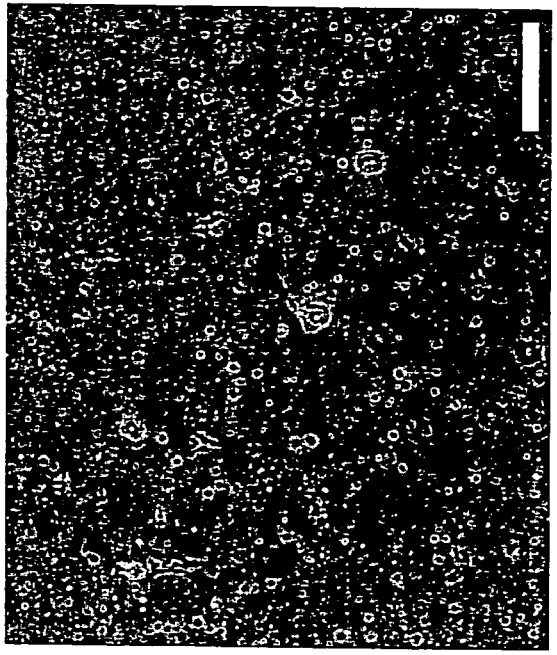
Hybridoma culture supernatant: No.23
Isolated human hepatocytes (49 yeas old)
At day 1 in culture
R2 fraction

Fig. 18/2
At day 8 in culture
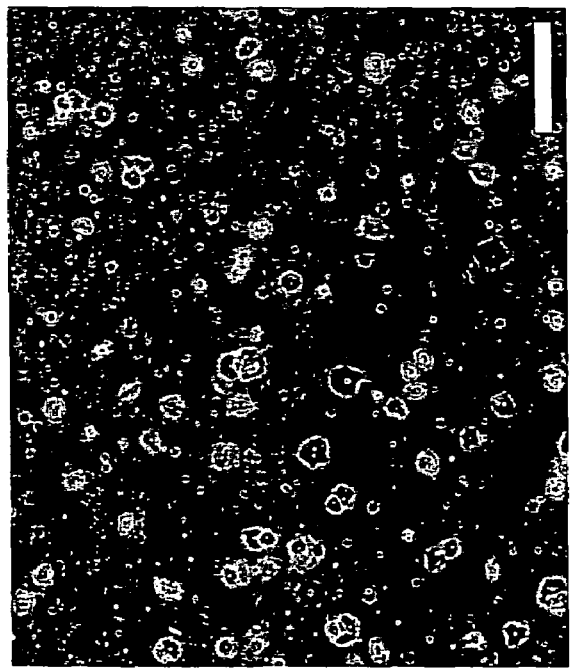
Hybridoma culture supernatant: No.23
Isolated human hepatocytes (49 yeas old)
At day 1 in culture
R3 fraction
Bar, 100 μm

SEQUENCE LISTING

```
<160> NUMBER OF SEQ ID NOS: 6

<210> SEQ ID NO 1
<211> LENGTH: 19
<212> TYPE: DNA
<213> ORGANISM: Artificial sequence
<220> FEATURE:
<223> OTHER INFORMATION: Synthesized oligonucleotide

<400> SEQUENCE: 1
gtcttggctc gctgcaatc                                                  19

<210> SEQ ID NO 2
<211> LENGTH: 19
<212> TYPE: DNA
<213> ORGANISM: Artificial sequence
<220> FEATURE:
<223> OTHER INFORMATION: Synthesized oligonucleotide

<400> SEQUENCE: 2
cgggagactg aggcaggag                                                  19

<210> SEQ ID NO 3
<211> LENGTH: 21
<212> TYPE: DNA
```

```
<213> ORGANISM: Artificial sequence
<220> FEATURE:
<223> OTHER INFORMATION: Synthesized oligonucleotide

<400> SEQUENCE: 3
ccgcctcctg ggttcaagcg a                                          21

<210> SEQ ID NO 4
<211> LENGTH: 19
<212> TYPE: DNA
<213> ORGANISM: Artificial sequence
<220> FEATURE:
<223> OTHER INFORMATION: Synthesized oligonucleotide

<400> SEQUENCE: 4
ggatgcaggg atgatgttc                                             19

<210> SEQ ID NO 5
<211> LENGTH: 19
<212> TYPE: DNA
<213> ORGANISM: Artificial sequence
<220> FEATURE:
<223> OTHER INFORMATION: Synthesized oligonucleotide

<400> SEQUENCE: 5
tgcaccacca actgcttag                                             19

<210> SEQ ID NO 6
<211> LENGTH: 22
<212> TYPE: DNA
<213> ORGANISM: Artificial sequence
<220> FEATURE:
<223> OTHER INFORMATION: Synthesized oligonucleotide

<400> SEQUENCE: 6
cagaagactg tggatggccc tc                                         22
```

METHOD OF PROLIFERATING HUMAN HEPATOCYTES AND METHOD FOR OBTAINING HUMAN HEPATOCYTES

This application is a U.S. national stage of International Application No. PCT/JP03/03623 filed Mar. 25, 2003.

TECHNICAL FIELD

The present invention relates to a method for proliferating human hepatocytes in a mouse body, a chimeric mouse carrying human hepatocytes in the liver thereof, a method for obtaining human hepatocytes from said chimeric mouse, and human hepatocytes obtained thereby. Human hepatocytes obtained from said chimeric mouse may be used as a material of a hepatocyte kit or an extracorporeal artificial liver.

BACKGROUND ART

A liver has 500 or more types of various specific functions. For example, major functions of a liver are plasma protein synthesis and excretion, blood sugar control by gluconeogenesis and glycogen metabolism, lipogenesis, ureogenesis, bile synthesis and excretion, detoxication and so on.

Most substances incorporated into a body are mainly metabolized in a liver. In the field of pharmaceutical development, what type of metabolism pharmaceutical candidate substances will be received in a liver and what type of effect is given to a liver or other organs and tissues are essential data. Further, many chemical substances have been synthesized and discharged into environment up to now. To elucidate what kind of effect these substances have exerted individually or in combination to a human body is socially very important. Toxicity test on liver functions are essential for evaluation of the effects of such chemical substances to a human body.

Mice, rats, rabbits, dogs, monkeys, etc are used at present for safety tests and drug metabolism tests of chemical substances including pharmaceutical candidate substances. Especially in pharmaceutical development, toxicological tests and safety tests using animals are compulsive before entering phase I study for human; therefore, long period and efforts as well as huge costs are required in these tests.

However, there is no guarantee that data obtained by these animal experiments can be applicable to human. In fact, many cases are known wherein a substance not recognized toxicity in animal experiments exhibited toxicity in human or vice versa. Consequently, it is expected up to now that development of many pharmaceutical candidate substances is aborted after entering in phase I study on human, and besides expected that there is many case wherein although a substance has actually no toxicity in human and the development thereof is aborted before entering a clinical trial due to exhibiting strong toxicity in animal experiments.

This may be caused by difference in metabolic functions in a human liver and metabolic functions in livers of mice and rats. Recently, in vitro metabolic tests and toxicity tests using human hepatocytes have been performed. However, amount of livers from brain death patients which were not used for transplantation and amount of human hepatocytes obtained from hepatectomy in tumor excision are far fewer than demanded. Consequently, development of technology for human hepatocyte proliferation is essential for pharmaceutical development.

Necessity of high amount of human hepatocytes is very much alike in an extracorporeal artificial liver. The artificial liver is medical device acting liver function artificially. It is vigorously in progress to develop a hybrid artificial liver combining with the artificial action based on physicochemical principle such as adsorption, dialysis and filtration, along with biological actions using perfusion of an excised liver and liver tissue. In such a development of an artificial liver, it is essential to improve membrane and circuit for enhancing physicochemical function, along with to supply high amount of hepatocytes applicable to human use.

However, in a case of human hepatocytes, it has been considered impossible to serially subcultivate primary cells, which are separated from matured individual. Namely, the matured hepatocytes with adhesion dependency are largely damaged when cells are detached from culture substrate for subcultivation operation and are difficult to re-adhere to culture substrate. Contrary to that, the present inventors of this application have invented the methods for proliferating hepatocytes, wherein small hepatocytes having clonal proliferative ability were isolated from normal hepatocytes separated from human liver, and further, it was carried out to primarily culture the small hepatocytes and then to subculture the cultured hepatocytes; and which were granted patents (JP-A-08-112092, JP No.3266766. U.S. Pat. No. 6,004,810; JP-A-10-179148, JP No.3211941; JP-A-07-274951, JP No. 3157984; and JP-A-09-313172, JP No.3014322).

Although the methods of those patented inventions provide new technique to obtain human hepatocytes in large scale by in vitro proliferation of hepatocytes, there remains a problem of diminishing some liver functions during long period subculture. Therefore, these cells obtained by the above-described methods are useful, for example, for a screening system of medical drug for maintaining liver function, or for a testing system of toxicity and efficacy of medical drugs in terms of certain functions remained after long period subculture, however, these cells are insufficient to use as substitution of human liver function, or for a material of a hybrid-type artificial liver.

As a measure to solve the above problems in proliferation of hepatocytes in vitro, a method for proliferating human hepatocytes in animal body (in vivo) has been proposed.

For example, Heckel, et al. prepared the albumin-urokinase-type plasminogen activator transgenic mouse (uPA-Tg mouse). In this mouse, as the urokinase plasminogen activator (uPA) gene is attached to an enhancer and a promoter of albumin, uPA protein is specifically expressed in a liver (Heckel J L, Sandgren E P, Degen J L, Palmiter R D, and Brinser R L; Neonatal bleeding in transgenic mice expressing urokinase-type plasminogen activator. Cell 62:447-456, 1990). The color of hepatocytes of said mouse looks white by naked eye due to injury by uPA protein, and some mice die by bleeding or liver failure. It has been known that when normal hepatocytes of lacZ transgenic mouse were transplanted into a spleen of the above-mentioned mouse, the transplanted hepatocytes are attached to the liver and proliferated, and finally the recipient hepatocytes are replaced by the donor hepatocytes (Rhim J A, Sandgren E P, Degen J L, Palmiter R D, and Brinster R L; Replacement of diseased mouse liver by hepatic cell transplantation. Science 263:1149-1152, 1994). Further, Rhim, et al. prepared the uPA-Tg/NUDE mouse by mating between the uPA-Tg mouse and a NUDE mouse which has no T-cell function due to hereditary deletion of thymus. A mouse having rat hepatocytes was prepared by transplantation of rat hepatocytes into the uPA-Tg/NUDE mouse (Rhim J A, Sandgren E P, Palmiter R D and Brinster R L; Complete reconstitution of mouse liver with xenogeneic hepatocytes. Proc. Natl. Acad. Sci. USA 92:4942-4946, 1995). However, there is no report on a chimeric mouse carrying human hepatocytes using said mouse.

Dandri, et al. prepared the uPA-Tg/Rag2 mouse by mating the uPA-Tg mouse and Rag2 mouse which is a knockout mouse having an immunodeficient characteristics. It has been reported that 15% of the mouse liver was replaced by human hepatocytes when human hepatocytes obtained from a human liver were transplanted into a liver of the uPA-Tg(+/−)/Rag2 mouse. Further they were succeeded in in vivo infection with hepatitis B virus to said mouse (Dandri M, Burda M R, Torok B, Pollok J M, Iwanska A, Sommer G, Rogiers X, Rogler C E, Gupta S, Will H, Greten H, and Petersen J; Repopulation of mouse liver with human hepatocytes and in vivo infection with hepatitis B virus. Hepatology 33:981-988, 2001).

Also, the inventors of this present invention have disclosed in a prior patent application (JP-A-2002-45087) that in a chimeric mouse produced by transplantation of human hepatocytes into an uPA-Tg/SCID mouse obtained by mating the uPA-Tg mouse and SCID mouse which is an immunodeficient mouse, the transplanted human hepatocytes have substantially taken place functions of a mouse liver. In this chimeric mouse of the prior invention, mouse hepatocytes have been dysfunctioned due to expression of uPA gene, and thus the liver function is maintained by the transplanted human hepatocytes. Therefore, said chimeric mouse is quite useful as an experimental animal for evaluating toxicity and efficacy of test substances because the in vivo function of transplanted human hepatocytes may be evaluated precisely. However, the chimeric mouse of the prior invention cannot live 50 days or longer after transplantation of human hepatocytes. Also, due to proliferation normalized mouse hepatocytes in the course of growing, proliferation efficiency of transplanted human hepatocytes was low and replacement ratio of human hepatocytes remained about 50%.

Above finding has also been supported by a recent report published by Mercer, et al. (Mercer D F, Schiller D E, Eliiott J F, Douglus D F, Hao C, Ricnfret A, Addison W R, Fischer K P, Churchill T A, Lakey J R T, Tyrrell D L J and Keteman N M; Hepatitis C virus replication in mice with chimeric human livers. Repopulation of mouse liver with human hepatocytes and in vivo infection with hepatitis B virus. Nature Medicine 7:927-933, 2001). Mercer, et al. have reported that the uPA-Tg/SCID mouse, prepared by similar procedures as described by the inventors of this present application, was transplanted with thawed human hepatocytes which had been stored in a frozen state; as the results, less than 2 mg/ml of human albumin was detected in mouse serum (equivalent to approximately less than about 1 mg/ml in blood) implying that about 50% of liver have been replaced by human hepatocytes.

As described above, a chimeric mouse which is prepared by a transplantation of human hepatocytes into an immunodeficient hepatopathy mouse (uPA-Tg/ SCID mouse) was insufficient as means to proliferate transplanted human hepatocytes in large scale in a mouse, even though a chimeric mouse itself had usefulness (for example, for in vivo testing of toxicity or efficacy to human hepatocytes).

Moreover, the chimeric mouse transplanted with human hepatocytes can not live for long period of time; and since mouse hepatocytes proliferate in a course of its growing, availability of such a chimeric mouse as an in vivo evaluation system of toxicity or efficacy against human hepatocytes has been limited.

Scope of the present invention is to provide, as a method for proliferating human hepatocytes, an improved method for proliferating human hepatocytes sufficiently in a mouse body.

Also, to provide a method for separation and recovery of human hepatocytes propagated in a mouse body by extension of life time is also included in the scope of the present invention.

Further, the scope includes to provide a method for obtaining a large number of chimeric mice carrying human hepatocytes with certain specifications by means of transplantation of separated human hepatocytes into plural mice and proliferation in mice bodies, and a method for obtaining human hepatocytes with certain specifications separated from said mouse in large scale.

Furthermore, to provide a method for application of separated human hepatocytes is also included in the scope.

In addition, the scope of the present application is to provide a useful monoclonal antibody useful to operate the above-described each invention, and a new hybridoma cell line producing said monoclonal antibody.

DISCLOSURE OF INVENTION

The present application provides, as the 1st invention to solve the above-described problems, method for proliferating human hepatocytes, which comprises transplanting human hepatocytes into a liver of an immunodeficient hepatopathy mouse, and then feeding the mouse transplanted with the human hepatocytes under such a condition as being protected from the attack by human complement produced by the human hepatocytes thereby proliferating the transplanted human hepatocytes in the mouse liver.

In a preferred embodiment of the method of the 1st invention, the condition of being protected from the attack by human complement is at least one of the following (a) and (b):
(a) the mouse transplanted with the human hepatocytes is administered at least once with a complement inhibitor;
(b) a progeniture mouse obtained by mating between an immunodeficient hepatopathy mouse and a decay-accelerating factor (DAF/CD55) transgenic mouse is utilized as the immunodeficient hepatopathy mouse.

Also, in the method of the 1st invention, a preferred embodiment is that the immunodeficient hepatopathy mouse is the progeniture mouse obtained by mating between a genetically immunodeficient mouse and a genetically hepatopathy mouse. Additionally, a preferred embodiment of the method is that the progeniture mouse is a hemizygous immunodeficient hepatopathy mouse, and this hemizygous immunodeficient hepatopathy mouse is administered with a hepatocyte growth inhibitor and then the human hepatocytes are transplanted therein.

Further, in the method of the 1st invention and preferred embodiments thereof described above, it is another preferred embodiment that the immunodeficient hepatopathy mouse transplanted with the human hepatocytes is administered with an anti-mouse Fas antibody.

Also, in the 1st invention the following each method is also a preferred embodiment, wherein the human hepatocytes to be transplanted into the immunodeficient hepatopathy mouse are proliferative human hepatocytes, and the proliferative human hepatocytes are human hepatocytes recognized by a monoclonal antibody which specifically recognizes human hepatocytes which proliferate, and the monoclonal antibody is one produced from Mouse-Mouse hybridoma K8223 (FERM BP-8334).

The present application provides, as the 2nd invention, a method for proliferating human hepatocytes in large scale, which comprises the following steps (1) to (3), and the steps (2) and (3) are repeated at least once;
(1) a step comprising transplanting human hepatocytes into a liver of an immunodeficient hepatopathy mouse, and then feeding the mouse transplanted with human hepatocytes under such a condition as being protected from the attack by human complement produced by the human hepatocytes thereby proliferating the transplanted human hepatocytes in the mouse liver;

(2) a step isolating the proliferated human hepatocytes from the mouse liver; and (3) a step comprising transplanting the human hepatocytes isolated from the mouse liver into the liver of an immunodeficient hepatopathy mouse, and then feeding the mouse transplanted with the human hepatocytes for not shorter than 50 days under such a condition as being protected from the attack by human complement produced by the human hepatocytes.

In preferred embodiments of the method of the 2nd invention, the condition of being protected from the attack by human complement in the step (1) and/or the step (3) is at least one of the following (a) and (b):

(a) the mouse transplanted with human hepatocytes is administered at least once with a complement inhibitor;

(b) a progeniture mouse obtained by mating between an immunodeficient hepatopathy mouse and a decay-accelerating factor (DAF/CD55) transgenic mouse is utilized as the immunodeficient hepatopathy mouse.

Also, in the 2nd invention, each of the following method is preferable, wherein the immunodeficient hepatopathy mouse in said steps (1) and/or (3) is the progeniture mouse obtained by mating between a genetically immunodeficient mouse and a genetically hepatopathy mouse; the progeniture mouse is a hemizygous immunodeficient hepatopathy mouse; and said hemizygous immunodeficient hepatopathy mouse is administered with a hepatocyte growth inhibitor and then human hepatocytes are transplanted therein.

Further, in the method of the 2nd invention and its preferred embodiments, another preferred embodiment is the immunodeficient hepatopathy mouse transplanted with human hepatocytes in said steps (1) and/or (3) is administered with an anti-mouse Fas antibody.

Also, in the 2nd invention, there are also preferred embodiments respectively, wherein the human hepatocytes to be transplanted into the immunodeficient hepatopathy mouse in the step (1) and/or the step (3) are proliferative human hepatocytes; the proliferative human hepatocytes are human hepatocytes recognized by a monoclonal antibody which specifically recognizes human hepatocytes which proliferate with forming colony; and the monoclonal antibody is one produced from Mouse-Mouse hybridoma K8223 (FERM BP-8334).

Furthermore, in the method of the 2nd invention, it is a preferred embodiment that only human hepatocytes are substantially isolated in step (2) by at least one of the following procedures (a) and (b);

(a) to treat a liver tissue separated from the mouse liver with collagenase; and (b) to isolate cells being recognized by a monoclonal antibody which specifically recognizes human hepatocytes but not recognizes non-human hepatocytes. In this embodiment, a more preferable embodiment is that the monoclonal antibody is one produced by Mouse-Mouse hybridoma K8216 (FERM BP-8333).

The present application provides, as the 3rd invention, a chimeric mouse carrying in the liver human hepatocytes proliferated by the above-described methods of the 1st invention or the 2nd invention.

Another preferred embodiment is that in the chimeric mouse of the 3rd invention, the proliferated human hepatocytes make up not less than 70% of the cells in the liver, and/or said mouse has human-type P450 activity.

The present application provides, as the 4th invention, a method for obtaining human hepatocytes comprises isolating the human hepatocytes from the liver of the chimeric mouse of the above-described 3rd invention.

Furthermore, in the method of the 4th invention, a preferred embodiment is that only human hepatocytes are substantially isolated by at least one of the following procedures (a) and (b);

(a) to treat a liver tissue separated from the mouse liver with collagenase; and (b) to isolate cells being recognized by a monoclonal antibody which specifically recognizes human hepatocytes but not recognizes non-human hepatocytes. And in this embodiment, a more preferable embodiment is that the monoclonal antibody is one produced from Mouse-Mouse hybridoma K8216 (FERM BP-8333).

The present application provides, as the 5th invention, the human hepatocytes obtained by the above-described method of the above-described 4th invention.

Further, the present application provides, as the 6th invention, a cellular kit containing the human hepatocytes of the above-described 5th invention.

Furthermore, the present application provides, as the 7th invention, a hybrid-type artificial liver filled with the human hepatocytes of the above-described 5th invention.

Furthermore, the present application provides, as the 8th invention, monoclonal antibody which specifically recognizes human hepatocytes but not recognize non-human hepatocytes. An example of the 8th invention is the monoclonal antibody produced from Mouse-Mouse hybridoma K8216 (FERM BP-8333).

Furthermore, the present application provides, as the 9th invention, a method for testing pharmaceutical kinetics or toxicity of a candidate substance, which comprises systemically administering the substance into the chimeric mouse of the above-described 3rd invention.

Embodiments, terms and concept described in the above each invention will be defined more in detail in the sections of Best Mode for Carrying Out the Present Invention or Examples. Various techniques required for operating the present invention may be available easily and precisely according to the known literature except for the techniques expressly provided with references, by those skilled in the art. For example, techniques of genetic engineering and molecular biology used in the present invention are described in the following literature; Sambrook and Maniatis, in Molecular Cloning-A Laboratory Manual, Cold Spring Harbor Laboratory Press, New York, 1989; Ausubel, F. M. et al., Current Protocols in Molecular Biology, John Wiley & Sons, New York, N.Y., 1995 et al.

BRIEF DESCRIPTION OF DRAWINGS

FIG. 5 is a graph showing correlations between human albumin concentration in mice blood and replacement rate by human hepatocytes, along with liver function.

FIG. 15 is a phase-contrast microscopic image of cultured human hepatocytes used as an antigen for preparing a monoclonal antibody.

FIG. 16 is an image of reactivity of hybridoma (K8223) culture supernatant on human hepatocytes observed by immunofluorescence staining.

FIG. 18 is a phase-contrast microscopic image in collection and culture of a cell population reacted (R2) and non-reacted (R3) with hybridoma (No. 23) culture supernatant).

BEST MODE FOR CARRYING OUT THE INVENTION

Figure 1:
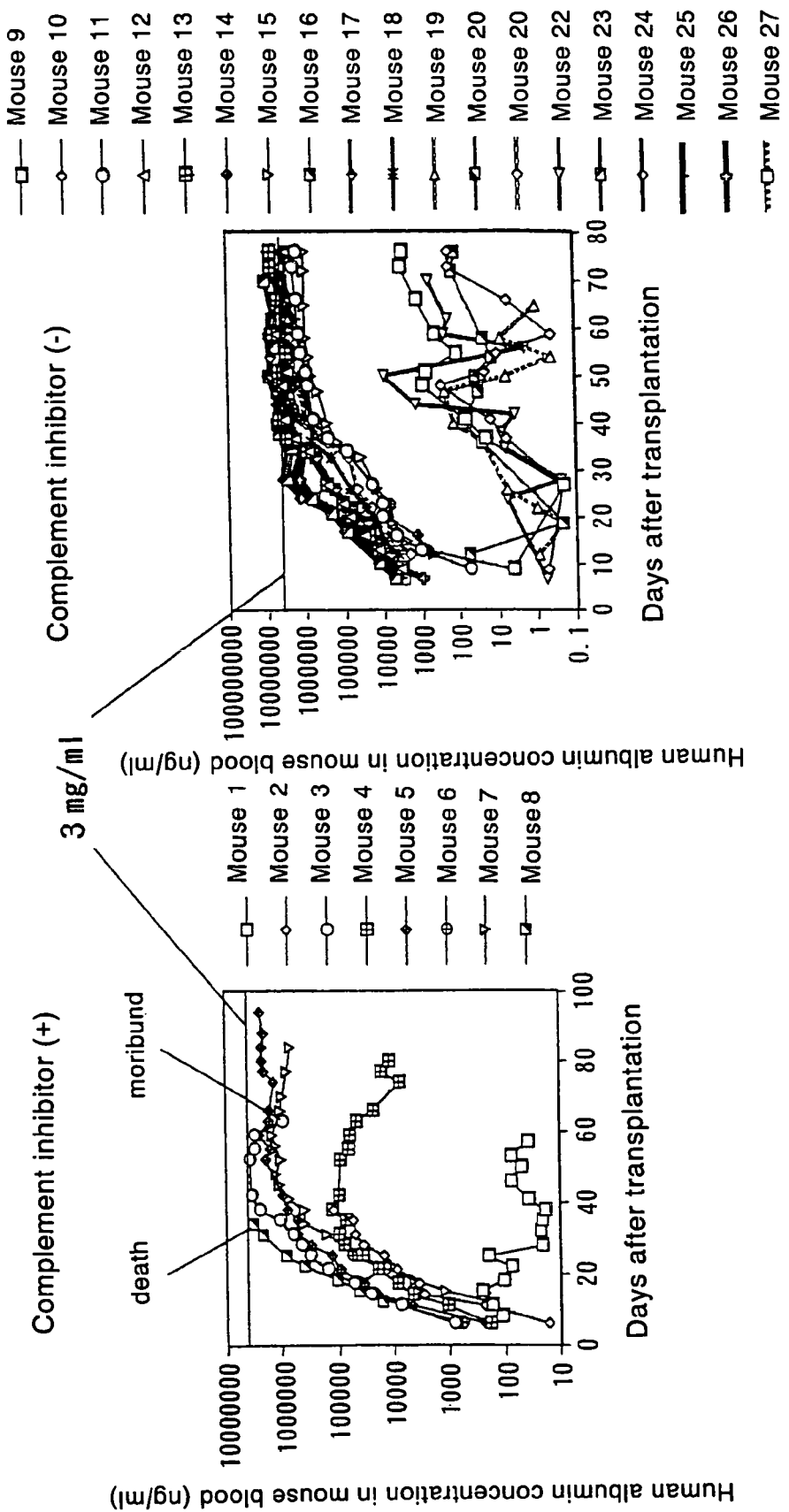
FIG. 1 is test result on the effect of a complement inhibitor on human albumin concentration.

The method for proliferating human hepatocytes of the 1st invention is characterized in that the transplanted human hepatocytes are proliferated in a mouse liver, wherein the human hepatocytes are transplanted into the liver of an immunodeficient hepatopathy mouse and then the recipient mouse is fed under such conditions as being protected from the attack by a human complement produced by the human hepatocytes.

As described above, Mercer, et al. have reported that they prepared an immunodeficient hepatopathy mouse (uPA-Tg/SCID mouse) and the thawed human hepatocytes stored at a frozen state were transplanted therein, and as the results, about 50% of the liver was replaced by the human hepatocytes (Nature Medicine 7:927-933, 2001). However, the human-hepatocytes-transplanted mouse prepared by Mercer, et al. could not achieve high replacement ratio by human hepatocytes.

The method of the 1st invention enables the human-hepatocytes-transplanted mouse to survive for not shorter than 50 days by protecting the mouse from the attack by the human complement produced by the transplanted human hepatocytes. Thus, extension of viable time of a mouse for not shorter than 50 days made possible for the mouse hepatocytes to be replaced by human hepatocytes by not less than 70%.

The 1st practical measure of protecting the recipient mouse from the attack by the human complement is administration of a "complement inhibitor" into a recipient mouse. An available complement inhibitor includes, for example, nafamostat mesilate (Futhan®, Torii Pharmaceutical Co., Ltd.), gabexate mesilate (FOY®, Ono Pharmaceutical Co., Ltd.), comostat mesilate (Foipan®, Ono Pharmaceutical Co., Ltd.), and cobra venom factor (cobra toxin). By the way, these complement inhibitors are medical drugs usually used at cell transplantation or organ transplantation, however, at ordinary operation of transplantation, the complement inhibitors are used to protect transplanted cells or organs from the attack by a complement produced by the liver of the recipient. On the other hand, in the present invention, as the recipient mouse is considered not to produce its own complement due to suffering from hepatopathy, a complement inhibitor is used to protect the recipient mouse from the attack by a complement produced by transplanted human hepatocytes.

The 2nd practical measure of protecting a recipient mouse from the attack by a human complement is the utilization of a progeniture mouse, as a recipient mouse, obtained by mating an immunodeficient hepatopathy mouse and a human decay-accelerating factor (hDAF/CD55) transgenic mouse. It has been reported that, in hDAF/CD55 transgenic mouse, hDAF protein expressed in high level on the surface of endothelial cells in such an organ as a kidney, a heart, a lung and a liver, and therefore, said mouse had tolerance against a human complement (Murakami H, Takahagi Y, Yoshitatsu M, Miyagawa S, Fujimura T, Toyomura K, Shigehisa T, Shirakura R, and Kinoshita T.; Porcine MCP gene promoter directs high level expression of human DAF (CD55) in transgenic mice. Immunobiology, 201:583-597, 1999/2000; van Denderen B J W, Pearse M J, Katerelos M, Nottle M B, Du Z-T, Aminian A, Adam W R, Shenoy-Scaria A, Lublin D M, Shinkel T A, and D'Apice A J F.; Expression of functional decay-accelerating factor (CD55) in transgenic mice protects against human complement-mediated attack. Transplantation, 61:582-588, 1996). Therefore, the recipient mouse which is a progeniture animal between an immunodeficient hepatopathy mouse and a human decay-accelerating factor (hDAF/CD55) transgenic mouse has high tolerance against a human complement produced by transplanted human hepatocytes. The hDAF/CD55 transgenic mouse may be prepared according to a well known method for producing a transgenic mouse (for example, Proc. Natl. Acad. Sci. USA 77:7380-7384, 1980) using a vector constructed according to the above-described literatures (Immunobiology, 201:583-597, 1999/2000; Transplantation, 61:582-588, 1996) to be able to express hHDAF under control of a promoter of, for example, a membrane cofactor protein (MCP) and H2K (b) (MHC class I) which have been expressed in wide variety of tissues and organs.

The "immunodeficient hepatopathy mouse" to be used for the method for proliferating human hepatocytes of the 1st invention is a "hepatopathy mouse" in which native hepatocytes are dysfunction, and also an "immunodeficient mouse" which does not reject transplanted cells from heterogeneous animals. Accordingly, the immunodeficient hepatopathy mouse maybe prepared by giving both hepatopathy- and immunodeficiency-inducing treatments to the same individual of mouse. The hepatopathy-inducing treatment includes, for example, a treatment with well known hepatopathy inducers (such as carbon tetrachloride, D-galactosamine, 2-acetylaminofluorene and pyrrolidine alkaloid) or a surgical hepatectomy, and the like. The immunodeficiency-inducing treatment includes administration of an immune suppressor and surgical thymectomy, and the like.

However, in the method of the 1st invention, a preferred embodiment is utilization of a progeniture mouse obtained by mating a mouse having genetic phenotype of hepatopathy and a genetically immunodeficient mouse as an immunodeficient hepatopathy mouse. For a genetically hepatopathy mouse, above-described uPA-Tg mouse produced by Rhim, et al. (Science, 263:1149 (1994)) may be exemplified. Alternatively, a transgenic immunodeficient hepatopathy mouse may be prepared using a gene to develop hepatopathy (for example, tissue-type plasminogen activator gene, and the like) according to a well known transgenic method (Proc. Natl. Acad. Sci. USA 77:7380-7384, 1980). Also, a gene bearing liver function (for example, a fumarylacetoacetate hydrase gene, and the like) may be knocked out according to a well known gene-targeting method (Science 244:1288-1292, 1989) to obtain a genetically hepatopathy mouse. On the other hand, as a genetically immunodeficient mouse, well known mouse, such as SCID mouse, NUDE mouse, RAG2 knockout mouse may be used. Hereinafter, a mouse obtained by the above procedures will be referred to as the "genetically immunodeficient hepatopathy mouse".

As to the genetically immunodeficient hepatopathy mouse, it is preferable to use a mouse having homozygote of a hepatopathy gene. In such a homozygous mouse, normal hepatocytes grow little, and therefore, proliferation of human hepatocytes is usually not inhibited by mouse hepatocytes. Note, however, that when mating is carried out between hemizygous mice, provability of obtaining such a homozygous mouse will be only 1/4.

On the other hand, a genetically immunodeficient hepatopathy mouse having a hemizygous hepatopathy gene (a "hemizygously immunodeficient hepatopathy mouse") may be obtained with probability of 1/2 by mating between hemizygous mice, or by mating a hemizygous mouse and SCID mouse. This case enables to perform the 1st invention by reduced cost. However, in the hemizygously immunodeficient hepatopathy mouse, since one of diploid chromosomes is normal gene, normal hepatocytes begin proliferation with forming colony because of deletion of hepatopathy gene, and at around 7 weeks after birth, normal mouse hepatocytes take over the mouse liver. Therefore, in general, the mouse hemizygously immunodeficient hepatopathy mouse is not suitable as a recipient mouse for proliferating human hepatocytes. And so, in the preferred embodiment of the 1st invention, before transplantation with human hepatocytes into the hemizygously immunodeficient hepatopathy mouse, a specific inhibitor for hepatocyte growth is administered to prevent from growth of normalized mouse hepatocytes to form colony. The hepatocyte growth inhibitor includes, for example, a kind of pyrrolidine alkaloids such as retrorsine, lasiocarpine, seneciphylline, monocrotaline and trichodesmine.

In the method of the 1st invention, human hepatocytes to be used for transplantation maybe isolated from a healthy human liver tissue according to a conventional method. A preferred embodiment, in particular, of the method of the 1st invention, is use of proliferative hepatocytes having active proliferation potential in vivo. By the way, in the present invention, "proliferative human hepatocytes" means human hepatocytes which form colonies as a single cell specie and proliferate so as to grow the colonies under in vitro culture condition. Such type of growth may sometimes be referred to as "clonogenic proliferation" because the colony forming cells are composed of a single cell specie. Further, such cells can increase the cell population by subculture.

As an example of such proliferative human hepatocytes, the human small hepatocytes invented by the present inventors of this application may be used. That is, the present inventors have found that the small hepatocytes having high proliferation potential are contained in a rat or human liver, and have applied for patents (JP-A-08-112092; JP No. 3266766; U.S. Pat. No. 6,004,810, JP-A-10-179148; JP No. 3211941, JP-A-7-274951; JP No. 3157984, JP-A-9-313172; JP No. 3014322). Relating articles thereof have been published (Tateno, C. and Yoshizato, K.; Growth and differentiation in culture of clonogenic hepatocytes that express both phenotypes of hepatocytes and biliary epithelial cells. Am. J. Phathol. 149: 1593-1605, 1996; Hino, H. Tateno, C. Sato, H. Yamasaki, C. Katayama, S. Kohashi, T. Aratani, A. Asahara, T. Dohi, K. and Yoshizato, K.; A long-term culture of human hepatocytes which show a high growth potential and express their differentiated phenotypes. Biochem. and Biophys. Res. Commun. 256: 184-191, 1999; Tateno, C. Takai-Kajihara, K.; Yamasaki, C. Sato, H. and Yoshizato, K.; Heterogeneity of growth potential of adult rat hepatocytes in vitro. Hepatology 31: 65-74, 2000; and Katayama, S. Tateno, C. Asahara, T. and Yoshizato, K.; Size-dependent in vivo growth potential of adult rat hepatocytes. Am. J. Pathol. 158: 97-105, 2001). Said human small hepatocytes grow rapidly in a recipient body, and can form a human hepatocyte population having normal liver function in short time due to superior proliferation potency.

Such small hepatocytes may be collected by the method using centrifugation described in the above prior inventions, or a method using a cell fractionator such as an elutoriator and FACS. Further, hepatocytes proliferating with forming colony can also be collected using a monoclonal antibody specifically recognizing them. The source of small hepatocytes may be in vitro proliferated human hepatocytes, stored hepatocytes in a frozen state, immortalized hepatocytes by introduction of such as a telomerase gene, and a mixture of these hepatocytes and non-parenchymal cells.

Another example of proliferative human hepatocytes includes human hepatocytes recognized by the monoclonal antibody (Example 6) specific for proliferative human hepatocytes. Such proliferative human hepatocytes recognized by a specific monoclonal antibody may be obtained in high purity by a well known method such as EIA, RIA and fluorescent antibody technique, depending on labels of the antibody. Concretely, separation of the proliferative human hepatocytes can be performed whereby a monoclonal antibody labeled with enzyme, radioisotope, magnetic beads or fluorescent pigment is brought into contact with a human hepatocytes population and hepatocytes indicating labeled signal are isolated. The enzyme used for labeling is not specifically limited, as long as it can satisfy conditions such as having large turnover number, exhibiting stability in a state of binding to an antibody and specifically coloring substrate; and includes enzyme generally used in EIA, such as peroxidase, β-galactosidase, alkaline phosphatase, glucose oxidase, acetylcholinesterase, glucose-6-phosphate dehydrogenase and malate dehydrogenase. An enzyme inhibitor and a coenzyme can also be used. Binding between these enzymes and the antibody can be achieved by a known method using a crosslinking agent such as a maleimide compound. With regard to substrate, known substance can be used depending on types of enzyme used. For example, when peroxidase is used as the enzyme, 3,3',5,5'-tetramethylbenzidine can be used, and when alkaline phosphatase is used as the enzyme, such as p-nitrophenol can be used. With regard to the radioisotope, conventionally used radioisotope in RIA such as $^{125}$I and $^3$H can be used. With regard to the fluorescence pigment, those conventionally used for fluorescence antibody technique such as fluorescence isothiocyanate (FITC) and tetramethylrhodamine isothiocyanate (TRITC) can be used. When a enzyme is used, detection of labeled signal can be performed by adding substrate, which develops color by decomposition due to enzyme action, followed by assaying enzyme activity by measuring the decomposed amount of the substrate by photometry, converting to an amount of bound antibody, and calculating the antibody amount by being compared with the standard value. When a radioisotope is used, radiation quantity emitted by the radioisotope is measured by using a scintillation counter, and the like. When a fluorescence pigment is used, fluorescence yield is measured by apparatus combined with a fluorescence microscope.

As described above, human hepatocytes, especially proliferative human hepatocytes, can be transplanted into an immunodeficient hepatopathy mouse via a mouse spleen, as described in the Example. Also, direct transplantation via a portal vein may be possible. Number of human hepatocytes to be transplanted may be approximately in the range from 1 to 10,000.

Further, in the preferred embodiment of the method of the 1st invention, an anti-mouse Fas antibody is administered into a mouse transplanted with human hepatocytes. An anti-mouse Fas antibody induces apoptosis by reacting with the Fas antigen on mouse hepatocytes. Administration of the anti-mouse Fas antibody into the mouse transplanted with human hepatocytes, causes mouse hepatocytes apoptosis, and leads them to die. Since this antibody does not affect human hepatocytes, only transplanted human hepatocytes may proliferate selectively. By this method, replacement ratio of human hepatocytes in mouse liver may further be increased.

A method for proliferating human hepatocytes in large scale in the 2nd invention will be explained next.

The method of the 2nd invention is characterized by carrying out the following steps (1) to (3).

Step (1): Human hepatocytes are proliferated in a mouse liver similarly as in the method of the 1st invention.
Step (2): Human hepatocytes proliferated in a mouse liver are isolated.
Step (3): The isolated human hepatocytes are transplanted respectively into immunodeficient hepatopathy mice, and the human hepatocytes are proliferated similarly as in the method of the 1st invention.

In addition, in the method of the 2nd invention, the above-described steps (2) and (3) are repeated at least once. That is, in the step (1), human hepatocytes transplanted into a mouse will increase the cell number up to 100 times in the mouse liver. Therefore, if all the proliferated human hepatocytes are recovered in the step (2), in principle, 100 mice may be transplanted with human hepatocytes at the step (3), and finally, human hepatocytes of 100×100 times initially transplanted human hepatocytes may be obtained. Further, by repeating the steps (2) and (3) twice, human hepatocytes of 100×100×100 times initially transplanted human hepatocytes may be recovered.

In the method of the 2nd invention, the step (1) and/or the step (3) may be conducted by the same procedures as in the above-described method of the 1st invention and a preferred embodiment thereof. The term above "and/or" means that one requirement in the method of the above-described 1st invention may be performed either in the step (1) only, or in the step (3) only, or in both steps (1) and (3). For example, in the step (1), proliferative human hepatocytes recognized by the above-described monoclonal antibody (the 8th invention) are transplanted into a mouse, and in the step (3), all of the recovered human hepatocytes may be used for transplantation. Each requirement in the above-described 1st invention may be selected appropriately depending on individual mouse in which human hepatocytes are proliferated, applications of the human hepatocytes recovered from a mouse, and the like.

The step (2) of the 2nd invention is a process where the proliferated human hepatocytes in the step (1) [the just before step, in the case when the steps (2) and (3) are repeated] are isolated from a mouse liver. As to the separation method, various methods (for example, a collagenase perfusion method, and the like) may be applied, however, application of at least one of the following methods (a) and (b) is preferable.

Method (a):

By treatment of a liver tissue separated from a mouse liver with collagenase, substantially only human hepatocytes are recovered. As cytotoxicity of collagenase is higher for mouse hepatocytes than for human hepatocytes, mouse hepatocytes may be damaged dominantly by controlling digestion period with collagenase, and only human hepatocytes may be collected. Treatment period by collagenase depends on ratio between human hepatocytes and mouse hepatocytes, however, for example, if content of human hepatocytes is not lower than 70%, treatment period may be from 8 to 20 minutes.

Method (b):

By isolation of cells recognized by a monoclonal antibody which specifically recognizes human hepatocytes but not recognizes non-human hepatocytes (the 8th invention), highly pure human hepatocytes are recovered. Such a monoclonal antibody may be exemplified by the monoclonal antibody produced by Mouse-Mouse hybridoma K8216 (FERM P-18751).

The 3rd invention of the present application is a "chimeric mouse" carrying human hepatocytes in the liver, wherein human hepatocytes are proliferated by the methods of the above-described 1st invention or 2nd invention. The chimeric mouse is preferably one lived not shorter than 50 days, more preferably not shorter than 70 days from transplantation of human hepatocytes. In addition, the chimeric mouse is preferably one, having replacement ratio of mouse liver by human hepatocytes is not lower than 70%, more preferably not lower than 90%, and particularly preferably not lower than 98%. Further, the chimeric mouse is one having human cytochrome P450 activity. That is, there are dozens of isozymes in human-type P450, such as CYP1A1, 1A2, 2C9, 2C19, 2D6 and 3A4, however, the chimeric mouse of the present invention is characterized by expressing these human-type P450 substantially in the same level as human hepatocytes. The cytochrome P450 is protein taking part in metabolism of ecdemic chemical substances in a liver, and therefore, a mouse liver expressing human-type P450 may metabolite chemical substances or the like substantially in similar manner as a human liver. Accordingly, the chimeric mouse of the 3rd invention enables a method for testing, for example, influence of efficacy or toxicity of medical drugs on human hepatocytes (the 9th invention). By the way, the prior invention of the present inventors (JP-A-2002-45087: chimeric animals) may be referred to on application of this kind of chimeric mouse. In addition, a population of a chimeric mouse carrying in the liver human hepatocytes proliferated in large scale by the method of the 2nd invention, is a population of chimeric mouse each carrying the same human-derived hepatocytes, and thus, enables to conduct a large-scale test under a substantially uniform condition.

The 4th invention of the present application is the method for isolating human hepatocytes from the chimeric mouse of the above-described 3rd invention. This method may be carried out similarly as in the step (2) of the above-described 2nd invention.

The 5th invention of the present application is human hepatocytes isolated from the liver of the chimeric mouse by the method for the above-described 4th invention. These human hepatocytes have substantially the same liver functions as normal hepatocytes in a human liver tissue by virtue of proliferating in an individual mouse. Accordingly, by application of the human hepatocytes of the 5th invention, a human hepatocytes kit (the 6th invention) which may be used for a drug metabolism test and a safety test, or a hybrid-type artificial liver (the 7th invention) may be provided. Further, using a module (a module filled with human hepatocytes) to be used for a hybrid-type artificial liver, valuable substances produced by human hepatocytes may be recovered.

As to a hepatocytes kit, various types of kits depending on cell species and applications are well known. Therefore, the cellular kit of the 6th invention may easily be prepared by those skilled in the art by adopting the human hepatocytes of the 5th invention and compositions of well known cellular kits. Also, as the compositions of modules and hybrid-type artificial organs are well known, it is easy for those skilled in the art to prepare the artificial liver of the 7th invention.

In addition, the 8th invention of the present application provides a monoclonal antibody which specifically recognizes human hepatocytes and does not recognize non-human hepatocytes.

This monoclonal antibody may be prepared according to well known method for preparation of a monoclonal antibody ("Monoclonal Antiobody" Nagamune H?. and Terada H.; Hirokawashoten, 1990; "Monoclonal Antiobody" James W. Goding, third edition, Academic Press, 1996), for example, according to the following procedures.

1. Preparation of Hybridoma Cells

Mammalians are immunized by using an immunogen containing subcultured human normal hepatocytes, and if necessary, animals are sufficiently sensitized by immunizing properly and additionally. Antibody producing cells (lymphocytes or spleen cells) are then collected from the animals to obtain hybrid cells between these antibody producing cells and myeloma cell lines. Cells which produce an objective monoclonal antibody are selected from these hybrid cell lines and cultured to obtain hybridoma cells. Each process is explained in detail below.

a) Preparation of an Immunogen

Human hepatocytes separated from normal liver tissues using collagenase are subcultured to prepare an immunogen. The human hepatocytes separated from human liver tissues not older than 15 years old, which are able to subculture for not less than 4 passages, preferably not less than 6 passages, are preferably used.

b) Immunization of Animals

Animals to be immunized can be mammals used for known hybridoma preparation and include typically, for example, mice, rats, goats, sheep, bovines and equines. Mice or rats are preferable animals for immunization from the standpoint of easy availability of myeloma cells to be fused with separated antibody producing cells. There is no specific limitation on strains of mice and rats actually used, and strains of mice such as A, AKR, BALB/c, BDP, BA, CE, C3H, 57BL, C57BR, C57L, DBA, FL, HTH, HT1, LP, NZB, NZW, RF, RIII, SJL, SWR, WB and 129, and strains of rats such as Low, Lewis, Sprague, Daweley, ACI, BN and Fisher can be used. Considering compatibility with myeloma cells, which will be explained hereinbelow, BALB/c strain for mouse and Low strain for rat are particularly preferable for animals to be immunized. Ages of these mice and rats for immunization are preferably 5-12 weeks old.

Immunization of animals can be performed by administering subcultured human hepatocytes as the immunogen, about $10^4$-$10^8$ cells, intracutaneously or intraperitoneally into the animals. Administering schedule of the immunogen depends on types of animals to be immunized, individual differences, etc., however generally frequency of administering the immunogen is 1-6 times and an administering interval is 1-2 weeks in case of multiple administrations.

c) Cell Fusion

Spleen cells or lymphocytes containing antibody producing cells are aseptically collected from the animals to be immunized after 1-5 days from the final immunization date on the above administering schedule. The separation of the antibody producing cells from spleen cells or lymphocytes can be performed according to a known method.

The antibody producing cells and the myeloma cells are then fused. The myeloma cells used are not specifically limited and can be selected appropriately from known cell lines for use. However, considering convenience in selection of hybridoma from the fused cells, use of HGPRT (Hypoxanthine-guanine phosphoribosyltransferase) deficient strain, wherein selection procedure thereof has been established, is preferable. Namely, those are X63-Ag8(X63), NS1-Ag4/1 (NS-1), P3X63-Ag8.U1(P3U1), X63-Ag8.653(X63.653), SP2/0-Ag14(SP2/0), MPC11-45.6TG1.7(45.6TG), FO, S149/5XXO, BU.1, etc. derived from mice; 210.RSY3.Ag.1.2.3(Y3), etc. derived from rats; and U266AR(SKO-007), GM1500·GTG-A12(GM1500), UC729-6, LICR-LOW-HMy2(HMy2), 8226AR/NIP4-1 (NP41), etc. derived from human.

Fusion of the antibody producing cells and the myeloma cells can be performed as appropriate under conditions without extremely reducing cell viability according to a known method. Such a method includes, for example, a chemical method for admixing the antibody producing cells and the myeloma cells in a high concentration solution of a polymer such as polyethylene glycol, and a physical method utilizing electric stimulation.

Selection of fused cells and non-fused cells are preferably performed, for example, by a known HAT (hypoxanthine-aminopterin-thymidine) selection method. This method is effective for obtaining fused cells by using the myeloma cells of HGPRT deficient strain which can not viable in the presence of aminopterin. Namely, fused cells with resistant to aminopterin can selectively be left and proliferated by culturing non-fused cells and fused cells in HAT medium.

d) Screening of Hybridoma

Screening of hybridoma cells producing an objective monoclonal antibody can be performed by known methods such as enzyme immunoassay (EIA), radio immunoassay (RIA) and fluorescent antibody technique. The hybridoma cells producing a monoclonal antibody specifically which recognizes human hepatocytes but not recognizes non-human hepatocytes can be obtained by such a screening method.

The screened hybridoma cells are cloned by known methods such as a methylcellulose method, a soft agarose method and a limiting dilution method and are used for antibody production.

The hybridoma cells obtained by methods explained hereinabove can be stored under a freezing state in liquid nitrogen or a freezer at not higher than −80° C. The present application provides Mouse-Mouse hybridoma K8216 (FERM BP-8333), as a typical example of such a hybridoma cell.

2. Obtaining a Monoclonal Antibody and Purification Thereof

A monoclonal antibody, which is specifically bound to human hepatocytes and never recognizes any non-human hepatocytes, can be obtained by culturing the hybridoma cells prepared in the above-described 1 with a known method.

A cultivation may be performed, for example, in medium having the same composition used in the above cloning method; or to obtain the monoclonal antibody in large scale, may be performed by a method wherein the hybridoma cells were intraperitoneally injected in mouse and the monoclonal antibody is collected from ascites.

Thus obtained monoclonal antibody can be purified, for example, by methods such as ammonium sulfate fractionation, gel filtration, ion exchange chromatography and affinity chromatography.

The present application provides the monoclonal antibody produced by the above-described hybridoma cell, Mouse-Mouse hybridoma K8216 (FERM BP-8333) as a typical example of the monoclonal antibody.

This monoclonal antibody of the 8th invention may be used for separating only human hepatocytes from a mouse liver in the above-described methods of the 2nd and the 4th inventions. Besides, since the monoclonal antibody of the 8th invention does not recognize non-human hepatocytes, said antibody may be used for isolating and purifying human hepatocytes when human hepatocytes are proliferated in a body of a non-human animal other than a mouse, or when non-human hepatocytes and human hepatocytes are mix cultured.

In addition, "a monoclonal antibody which specifically recognizes proliferative human hepatocytes" used in the present invention may also be prepared by the same method as described above (see Example 6), except for selecting a hybridoma producing an objective antibody, in a screening process. The present application provides the monoclonal antibody produced by Mouse-Mouse hybridoma K8223 (FERM BP-8334) as a typical example of such a monoclonal antibody.

Mouse-Mouse hybridoma K8223 was deposited under the Budapest Treaty on the International Recognition of the Deposit of Microorganisms. The hybridoma was deposited (Accession No. FERM P-I8752) on Mar. 6, 2002, and was subjected to international deposition on Mar. 20, 2003 (Accession No. FERM BP-8334). The deposit was made at the International Patent Organism Depositary, National Institute of Advanced Industrial Science and Technology, AIST Tsukuba Central 6, 1-1, Higashi 1-Chome Tsukuba-shi, Ibaraki-ken 305-8566 Japan.

EXAMPLES

Some tests exemplifying the present invention are described below; however, the scope of the present invention should not be limited thereto.

Example 1

Preparation of a Chimeric Mouse Carrying Proliferated Human Hepatocytes

A chimeric mouse carrying proliferated human hepatocytes in the liver was prepared by transplanting human hepatocytes into the liver of an immunodeficient hepatopathy mouse. Materials and methods for the preparation and the results of the relevant testing were as follows:

1. Materials (a) an albumin-urokinase plasminogen activator transgenic mouse (uPA-Tg): B6SJL-TgN (Alb1Plau) 144Bri
(b) SCID mouse (Scid): C.B-17/Icr Scidjcl
(c) nafamostat mesilate
(d) retrorsine
(e) human hepatocytes The mouse (a) and the mouse (b) were purchased from The Jackson Laboratory and CLEA Japan. Co., respectively. The medical agent (c) (brand name: Futhan®) and (d) were purchased from Torii Pharmaceutical and SIGMA Co., respectively.

The cells (e) were prepared as described below. Before operating hepatectomy, agreement to the informed consent by patient was completed. A normal liver tissue obtained from the removed liver was perfused with UW solution, and then transported at 4° C. The normal liver tissue was treated with collagenase to obtain a dispersed solution of a liver, followed by low-speed centrifugation (50×g, for 2 minutes) to separate precipitate and supernatant, washing the cells contained in each part (supernatant: small hepatocytes, precipitate: parenchymal hepatocytes) with culture medium and respectively counting cell number. When cells were stored in a frozen state, freeze-preservation liquid (from KURABO Co.) was added and then frozen using a programmed freezer. The frozen hepatocytes from the precipitate and the supernatant, stored in liquid nitrogen, were thawed at 37° C. in a constant temperature water bath, and cell number was counted. Cell concentration was adjusted to $4 \times 10^7$ cells/ml using medium just before transplantation.

2 Methods and Results 2.1 Preparation of a Mouse Suffering from Immunodeficient Hepatopathy The uPA-Tg mouse (hemizygote, +/−) and the SCID mouse (homozygote, +/−) were mated, and Tg(+/−)/SCID (+/−) mouse having phenotype of both parents was obtained in 35.2% probability. Identification of Tg(+/−) and Tg(−/−) was performed by a genome PCR method using a primer with a specific sequence for Tg gene. Also, identification of SCID (+/−) and SCID(−/−) was performed by PCR-RFLP method.

Thus obtained Tg(+/−)/SCID(+/−) mouse was then back-crossed with the SCID(+/+) mouse, to obtain Tg(+/−)/SCID (+/+) mouse. As the results, Tg(+/−) emerged in 37.9% probability and SCID(+/+) emerged in 52.8% probability. The objective Tg(+/−)/SCID(+/+) and Tg(+/+)/SCID(+/+) mice were obtained by mating Tg(+/−) /SCID(+/+) mice themselves.

Identification of homozygote and heterozygote of uPA genes was performed by the following method.

From 5 mm of a tail cut off from 8 to 10 days old mouse, genomic DNA was extracted using the Qiagen DNeasy Tissue Kit. Concentration and purity of the extracted DNA were measured using a spectrophotometer. To a mixture of 25 µl of master mix, 1 µl of primer F, 1 µl of primer R and 1 µl of Taqman probe, DNA and distilled water were added, and the total volume was adjusted to 50 µl to be subjected to quantitative PCR (ABI 7700, Sequencer Detector, PE Applied Biosystems).

The primers and Taqman probe were designed for directing to human growth-hormone-encoding sequence incorporated in a vector for uPA gene transfer as shown below.

```
Primer F:       gtcttggctcgctgcaatc     (SEQ ID No: 1)

Primer R:       cgggagactgaggcaggag     (SEQ ID No: 2)

Taqman probe:   ccgcctcctgggttcaagcga   (SEQ ID No: 3)
```

As a control, the following primer and Taqman probe directing to mouse G3PDH-encoding sequence were used.

```
Primer F:       ggatgcagggatgatgttc     (SEQ ID No: 4)

Primer R:       tgcaccaccaactgcttag     (SEQ ID No: 5)

Taqman probe:   cagaagactgtggatggccctc  (SEQ ID No: 6)
```

The PCR was carried out under the condition that after denaturation at 95° C. for 10 minutes, 50 cycles of denaturation at 95° C. for 15 seconds and elongation at 60° C. for 1 minute were repeated. From the relative value obtained by dividing the amount of amplified fragment of human growth-hormone-encoding sequence by the amount of amplified fragment of mouse G3PDH-encoding sequence as an internal control, the amount of introduced gene in genomic DNA is compared. A standard curve was obtained from sequential dilution of heterozygous or homozygous genome of a sample mouse, and the relative value of a mouse used for the standard curve was defined as 1. If the standard mouse is heterozygous one, a heterozygous mouse shows close value to 1 and a homozygous mouse shows close value to 2. However, if the standard mouse is homozygous one, a homozygous mouse shows close value to 1 and a heterozygous mouse shows close value to 0.5. From naked eye observation at anatomy, the hitting ratio is supposed to be about 90%.

2.2 Transplantation of Human Hepatocytes into the uPA-Tg/SCID Mouse

The Tg(+/+)/SCID(+/+) mouse, from 14 to 48 days old, was anesthetized by ether and incised about 5 mm at the flank, and then, from 10 to 12.5 µl of cell suspension with concentration from 4 to 8 ×10$^7$cells/ml (from 4 to 10×10$^5$ cells in total) was inoculated from a spleen head, and then stanched. As a hemostatic agent, 40 µl of an e-aminocaproic acid (SIGMA) solution (0.02 g/ml) was administered into the abdominal cavity, and then, after the spleen was returned to the abdominal cavity, the flank was sewed up. Concentration of uPA in mouse blood is high, because the uPA produced by hepatocytes of a Tg mouse is secreted extracellularly. The uPA has activity of catalyzing proteolysis and activation of plasminogen to plasmin, and decomposing fibrin clot. Hence, it has been said that a number of mice will die with bleeding in an intestinal duct and an abdominal cavity within 4 days after birth. To avoid death by bleeding on surgery, e-aminocaproic acid was administrated, which has hemostatic effects by inhibiting actions of a plasminogen activator and a plasmin.

The SCID/C.B-17 mouse used for mating is known to have neither T-cells nor B-cells but have NK cells. Therefore, to protect the transplanted human hepatocytes from the attack by NK cells, an asialo GM1 antibody which inhibits NK activity was inoculated into an abdominal cavity the day before and the day after transplantation. The progeniture of mouse was weaned at 4 weeks after birth, and each male and female was fed in a separate cage after 5 weeks.

2.3 Monitoring of Human Albumin in Mouse Blood

From 1 week after transplantation of human hepatocytes, 10 µl blood samples were taken from the tail of a mouse once or twice per a week, and concentration of human albumin was measured using Quantitative ELISA immunoassay (Bethyl Laboratories Inc.).

Increased concentration of human albumin in blood was observed in 11 mice out of 19 Tg(+/+)/SCID mice which had been transplanted with human hepatocytes (FIG. 1). The highest value was over 8 mg/ml corresponding to 62% of total albumin in mouse blood.

Figure 2:
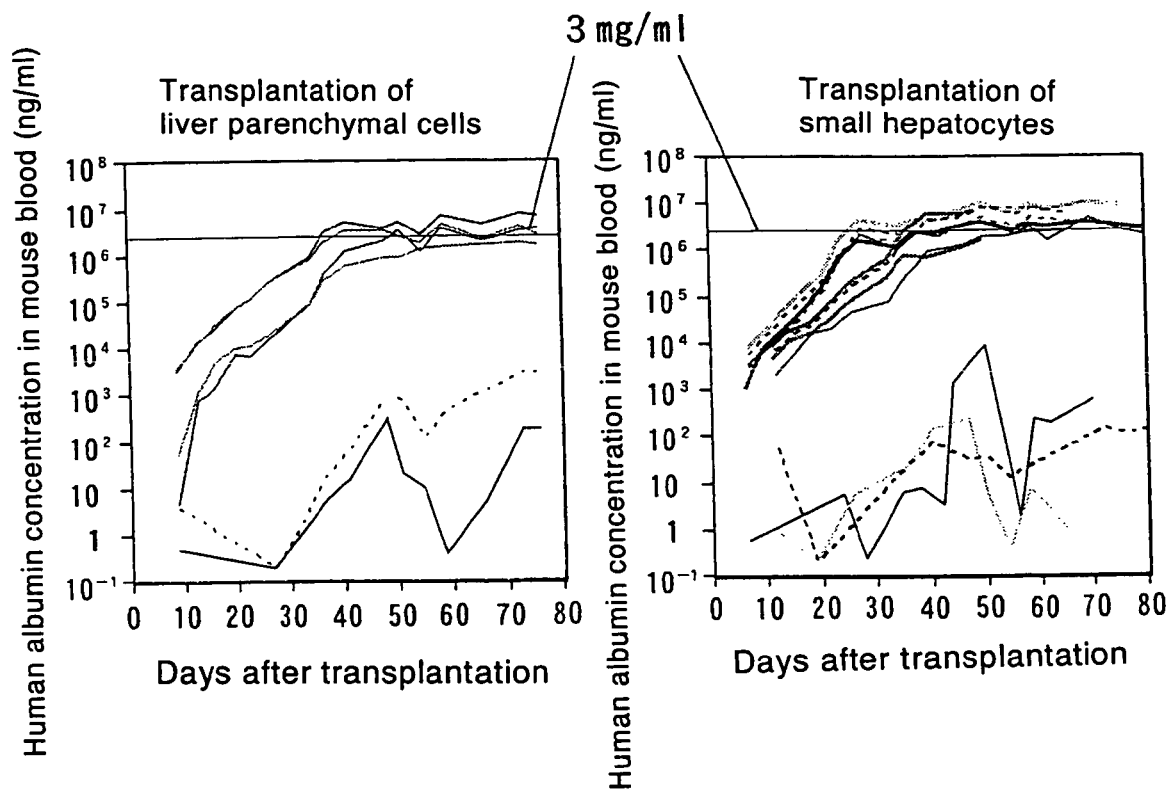
FIG. 2 is measuring result of blood albumin concentration in mice transplanted with human liver parenchymal cells or small hepatocytes.

Further, human albumin concentrations in blood were compared between mice transplanted with cells in supernatant (small hepatocytes) and mice transplanted with cells in precipitate (parenchymal hepatocytes) separated by low speed centrifugation of human hepatocytes. Higher increase in human albumin was observed in the mice transplanted with the small hepatocytes than those with the parenchymal hepatocytes (FIG. 2).

Figure 3:
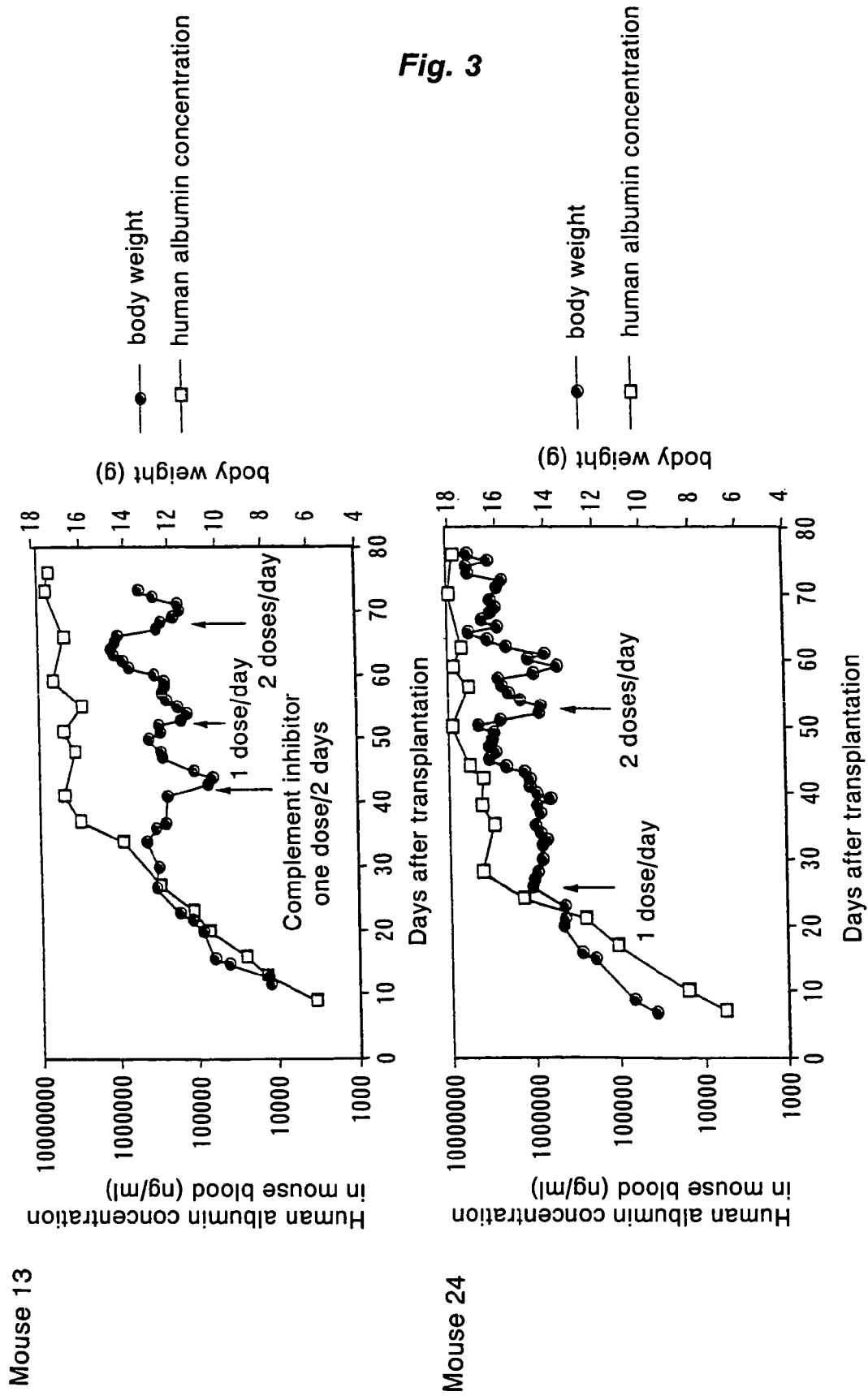
FIG. 3 is test result on the effect of a complement inhibitor on mice body weight.

2.4 A Human Complement Produced by Human Hepatocytes and Administration of a Complement Inhibitor Increase in concentration of human albumin in blood over 3 mg/ml was observed in mice which rapidly worsen mouse condition and led to death (FIG. 1). In the dead mice, bleeding was observed in lungs thereof, and affects of a complement produced by human hepatocytes were envisaged. Also, human hepatocytes in the mouse liver tissue were stained immunologically using an anti-human complement C3 antibody, and presence of a complement C3 in human hepatocytes was confirmed. Therefore, 200 µl of a complement inhibitor (Futhan®) with concentration of 2 mg/ml was administered into the mouse with increased human albumin concentration. Administration frequency was started from once per 2 days. Change in body weight was checked every day, and administration frequency or dose was increased when decrease in body weight was observed (FIG. 3). As the results, the mice with human albumin concentration in blood over 2 mg/ml received the complement inhibitor (Futhan®) every 2 days, and those over 4 mg/ml received every day, and further, those over 6 mg/ml received twice a day (FIG. 3). By this treatment, mouse could live for long period even when human albumin concentration in blood exceeded 3 mg/ml, and the highest detectable level of human albumin in blood was 8 mg/ml (FIG. 1).

Figure 4:
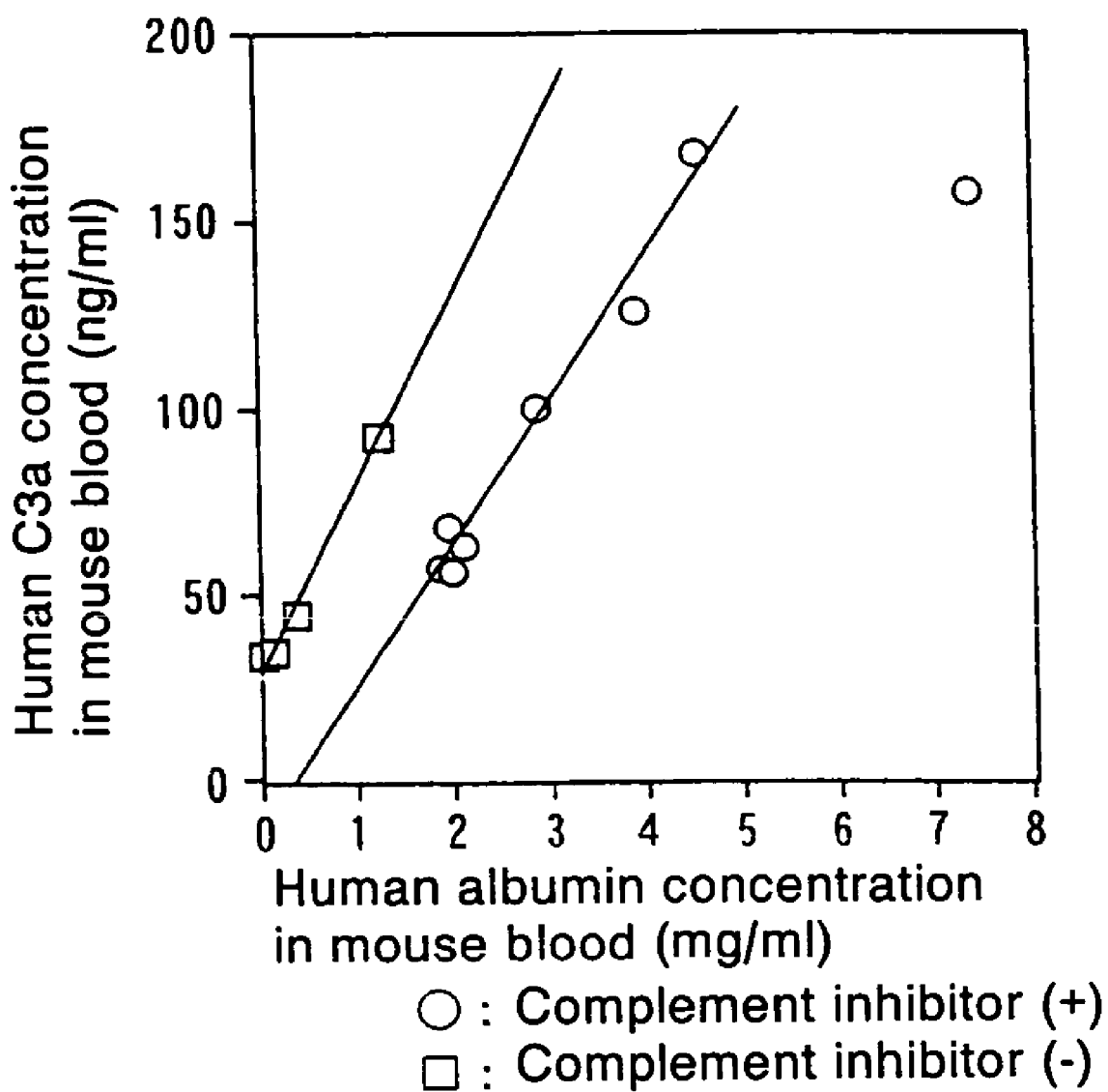
FIG. 4 is comparison on human complement (hC3a) concentrations between a complement inhibitor is administered and not administered in chimeric mouse.

Further, concentration of the human complement (hC3a) in blood of chimeric mice administered or non-administered with the complement inhibitor (Futhan®) was measured by ELISA method. In consequence, it was confirmed that hC3a concentration was lower in chimeric mice administered with the complement inhibitor compared with non-administered mice (FIG. 4).

2.5 Administration of Vitamin C and Serum of SCID Mouse

Possibility of vitamin C deficiency was considered in mouse having a liver replaced with human hepatocytes because human hepatocytes can not synthesize vitamin C. Therefore, ascorbic acid 2-phosphate dissolved in drinking water in 1 mg/ml was given to the mouse transplanted with human hepatocytes (by referring to "A method for feeding a rat with deficiency of ascorbic acid synthesis"; CLEA Japan Co.).

Further, a human hepatocytes-transplanted Tg(+/+)/SCID mouse showed slower increase in body weight and worse hair appearance, compared with a Tg(+/−)/SCID mouse. As it was considered that proteins, enzymes and the like synthesized by human hepatocytes in a mouse liver were insufficient for growth and maintenance of mouse body, 50 µl of SCID mouse serum was administered subcutaneously once per a week.

Increase in body weight of Tg(+/+)/SCID administered with SCID mouse serum was higher compared with non-received mice.

2.6 Gross and Histopathological Examination of a Mouse Liver

Blood was collected from a mouse under anesthesia with ether to measure serum albumin and GPT value. A liver and a spleen were removed to measure weight, followed by photographing, sampling for a frozen section block and a paraffin section block and extracting a microsomal fraction from the rest of the samples. Increase in human albumin concentration, along with increase in serum albumin and decrease in GPT value were observed (FIG. 5).

In mice with high human albumin value, whole liver looked pinkish, but in some mice, remaining white spot, which is a distinctive phenotype of Tg(+/+)/SCID, was observed. Also, there observed red color part in the liver, which part was considered as normalized mouse hepatocytes caused by deletion of introduced uPA gene.

Figure 6:
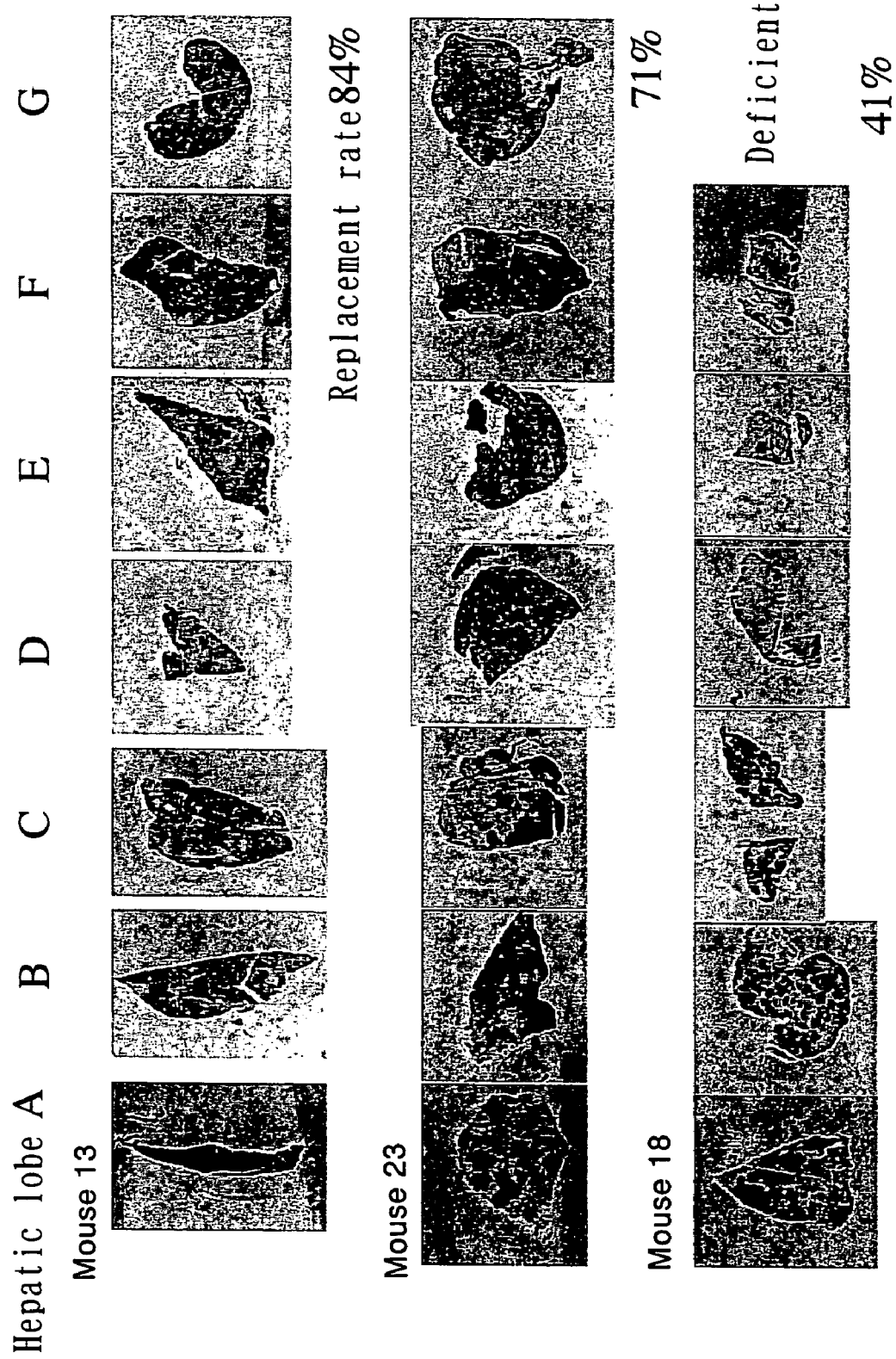
FIG. 6 shows images of immunostaining by a human specific cytokeratin 8/18 antibody.
Figure 7:
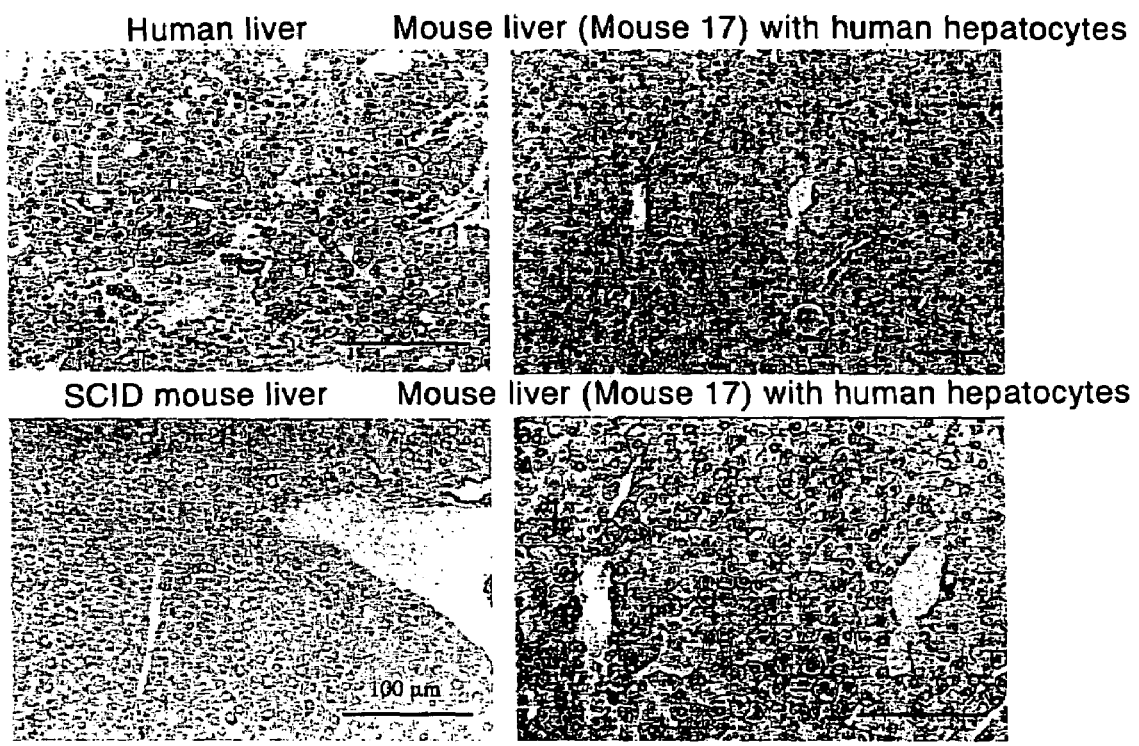
FIG. 7 shows magnified images of immunostaining by a human specific cytokeratin 8/18 antibody.

Frozen sections of each lobe of the liver were prepared, followed by reacting with the human specific cytokeratin 8/18 antibody (from ICN Pharmaceuticals, Inc., Ohio) and staining by peroxidase labeled DAKO Envision+™ (from DAKO Corporation, CA). With respect to each lobe of the liver, ratio of cytokeratin 8/18 positive areas in the total section area was calculated (FIG. 6, FIG. 7). In mice with high human albumin value, a percentage of the area of cytokeratin 8/18 positive hepatocytes was high. A mouse having over 80% of positive cells was also observed.

2.7 Analysis of P450 Isozymes in Microsome

Figure 8:
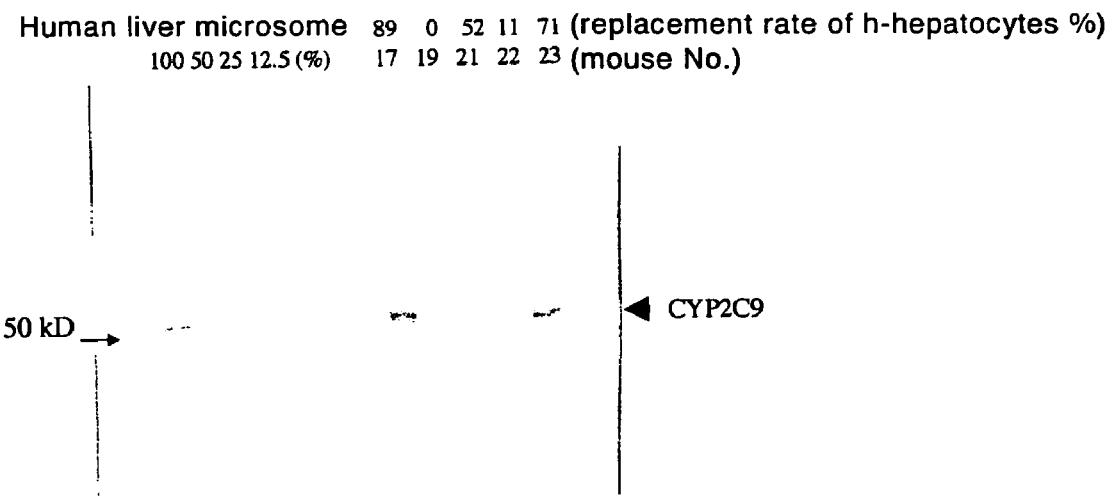
FIG. 8 is Western blotting analysis result of human specific CYP2C9 in microsomes from mouse liver transplanted with human hepatocytes.

Expression of P450 isozymes in a microsomal fraction collected from a mouse was detected by western-blotting analysis using antibodies which specifically recognize the P450 isozyme (from Daiichi Pure Chemicals Co., Ltd.). Expression of CYP2C9, a human specific P450 isozymes, was observed in mice with high human albumin value (FIG. 8).

Figure 9:
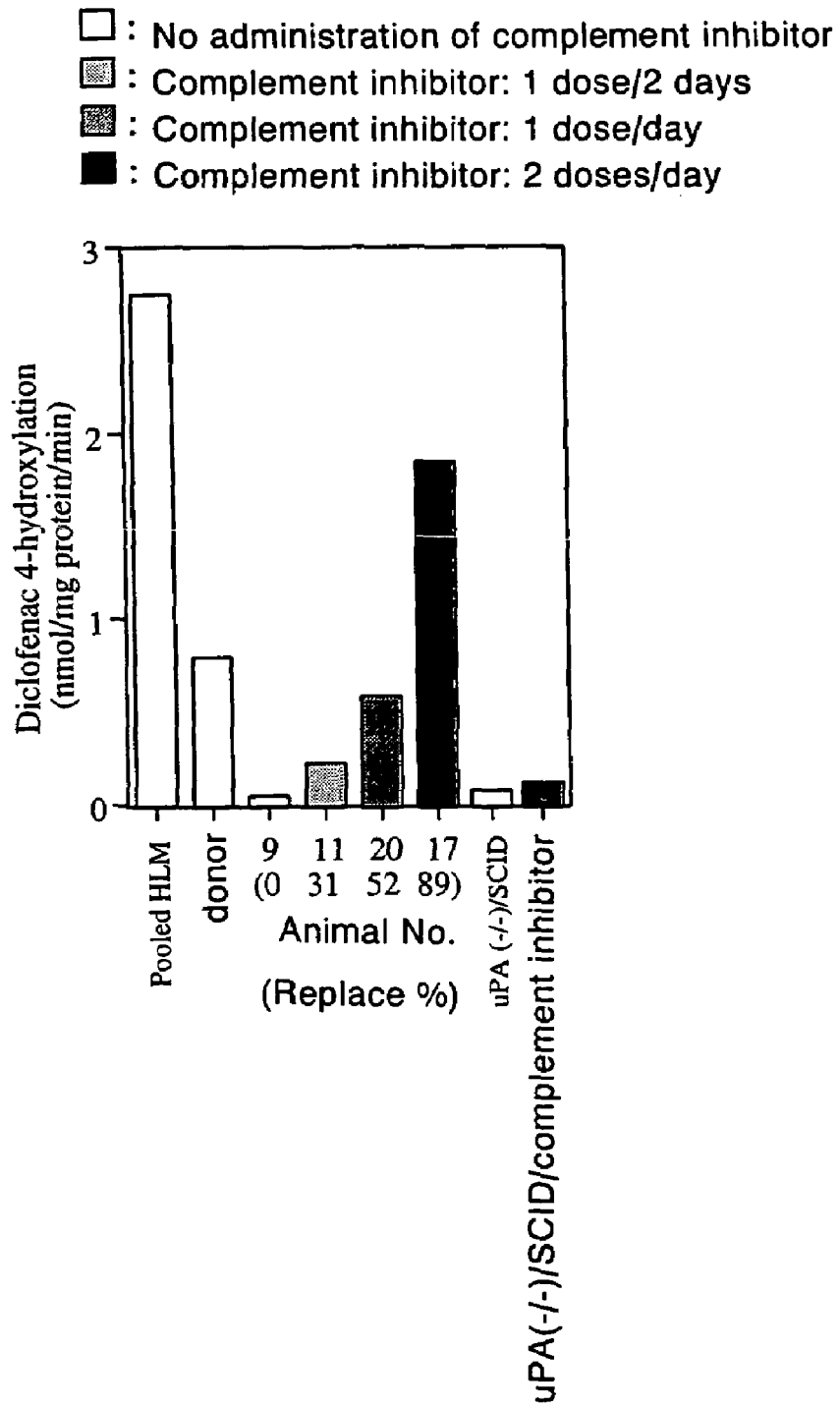
FIG. 9 is a graph showing metabolic activity of diclofenac in mouse or donor liver microsomes.

Further, to check activity of CYP2C9 in the microsomal fraction sampled from a mouse, diclofenac 4-hydroxylation activity was measured by adding diclofenac to the microsome. In consequence, diclofenac 4-hydroxylation activity was little detected in the uPA(−/−)/SCID mouse, and induction of activity by administration of a complement inhibitor was not observed also. On the other hand, in human-hepatocytes-transplanted chimeric mice, higher diclofenac 4-hydroxylation activity was observed with increase in replacement ratio of human cells. In a chimeric mouse with 89% of replacement ratio, diclofenac 4-hydroxylation activity was confirmed higher than that of donor (human) microsome (FIG. 9).

Figure 10:
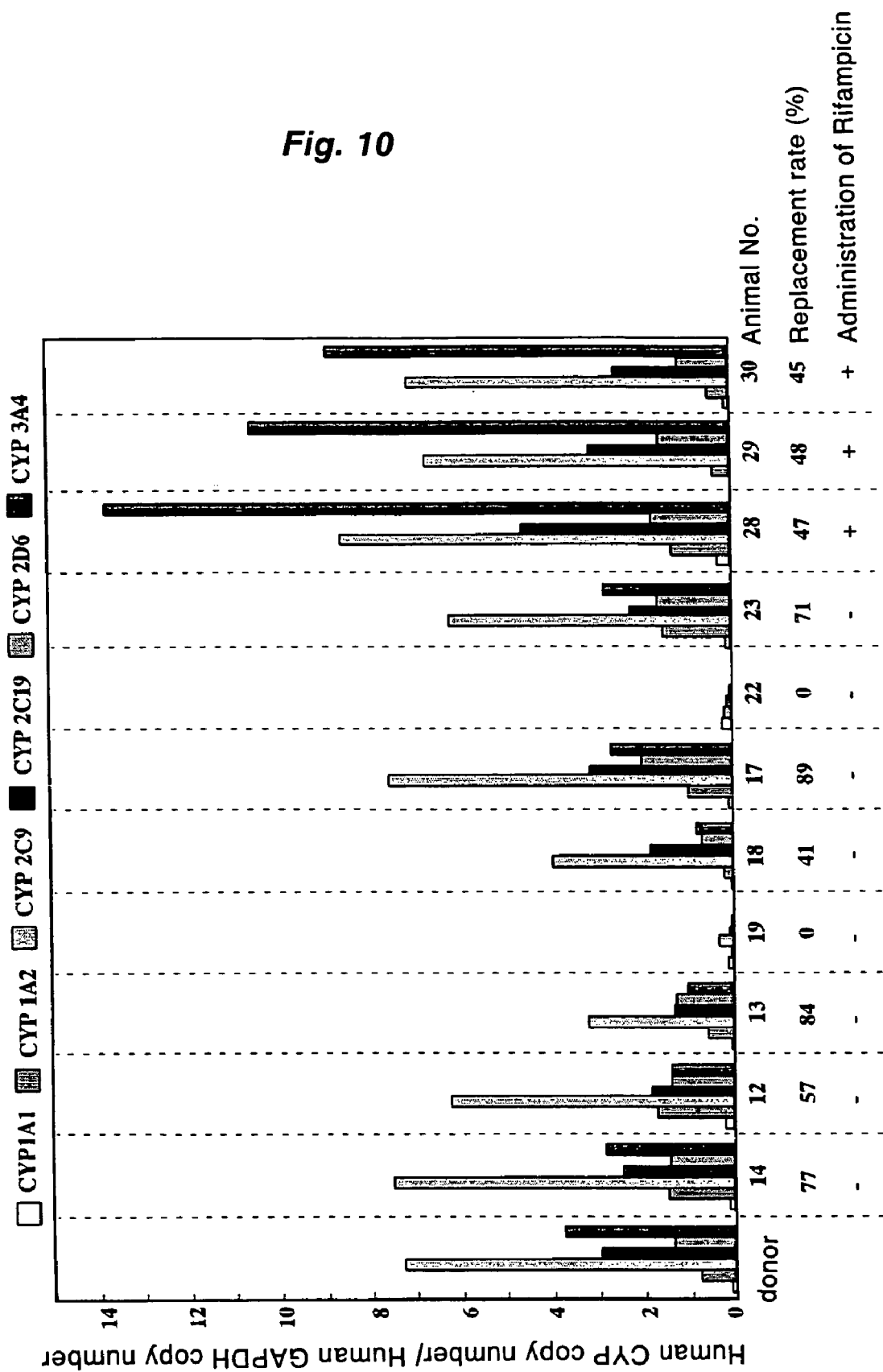
FIG. 10 is a graph showing expression amount of six types of human P450 isozymes in a chimeric mouse liver with various replacing rates of human hepatocytes and in chimeric mouse liver administered with rifampicin.

2.8 Expression of mRNAs of Respective P450 Isozymes in a Liver of a Chimeric Mouse, and Induction by Rifampicin Total RNA was extracted from a chimeric mouse, and corresponding cDNA was synthesized by reverse transcription reaction. Primers for 6 types of cDNA corresponding to each P450 is ozyme(CYP1A1, 1A2, 2C9, 2C19, 2D6 and 3A4)-encoding gene were synthesized, to measure expression of mRNA corresponding to each isozyme, using PRISM 7700 Sequence Detector (from Applied Biosystems Inc.). Consequently, a control mouse with replacement ratio of 0% expressed almost zero human-type P450, however, all of human-type P450 isozymes were expressed in a chimeric mouse liver, and the expression pattern was closely resembled to that of a donor (human) (FIG. 10).

Further, 3 chimeric mice were administered intraperitoneally with Rifampicin (50 µg/kg body weight) for 4 days, followed by taking out the liver at 5 days and assaying the expression of 6 human-type P450 similarly as described above. It is well known that Rifampicin induces expression of only human CYP3A4. As the result, the expression level of human-type CYP3A4 in the liver of the Rifampicin-administered chimeric mice were about 5.7 times higher compared with that of non-administered mice (FIG. 10).

Example 2

Separation of Human Hepatocytes from a Chimeric Mouse, and Purification of Human Hepatocytes with a Monoclonal Antibody From the chimeric mouse prepared in Example 1, hepatocytes were separated by a collagenase perfusion method. Concentration of collagenase was 0.05%, and treating period was 9 minutes. It was conceivable that hepatocytes was a mixture of human hepatocytes and mouse hepatocytes, however, most of hepatocytes separated (about 80%) were human hepatocytes because cytotoxicity of collagenase is higher for mouse hepatocytes than for human hepatocytes.

Further, to increase purity of human hepatocytes, only human hepatocytes were isolated using a mouse monoclonal antibody (the monoclonal antibody produced by the hybridoma K8216 in Example 6) which does not recognize mouse hepatocytes but specifically recognizes surface of human hepatocytes. The hepatocytes separated by collagenase perfusion, which contains about 80% of human hepatocytes, were reacted with the above-described antibody, followed by reaction with an FITC-labeled mouse IgG antibody and separation of cells reacted with the FITC-labeled mouse IgG antibody, using fluorescence activated cell sorter (FACS). As the result, purity of human hepatocytes went up to not lower than 95%.

Example 3

Figure 11:
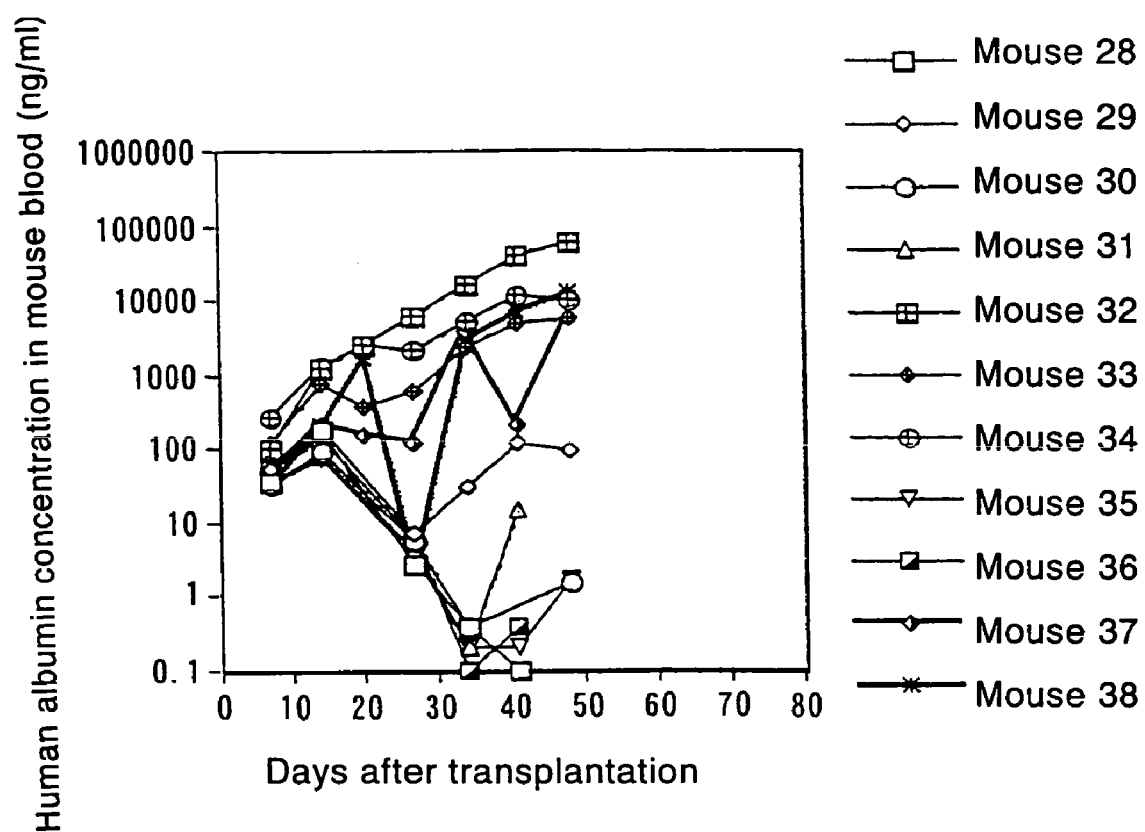
FIG. 11 shows test result on human albumin concentration in mice blood from mice re-transplanted with human hepatocytes.

Re-transplantation of Human Hepatocytes Isolated from a Chimeric Mouse into a uPA-Tg/SCID Mouse The hepatocytes isolated in Example 2 were transplanted into another uPA-Tg(+/+)/SCID mouse, and the transplanted mouse was fed similarly as in Example 1. As the result, increase in human albumin level in mouse blood was observed (FIG. 11).

Example 4

Figure 12:
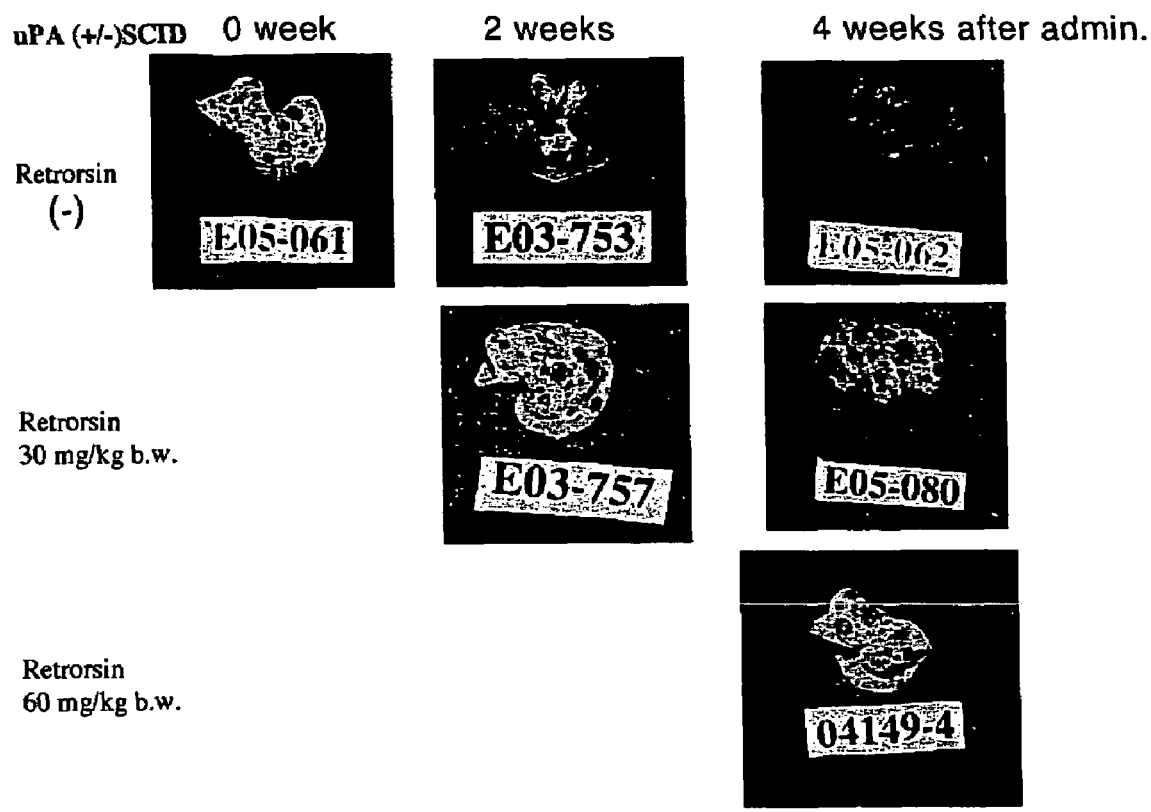
FIG. 12 is test result on the effect of retrorsine administering in uPA(+/+)/SCID mice.

Growth Inhibition of Normalized Mouse Hepatocytes Caused by Deletion of Introduced uPA Gene Retrorsine was inoculated intraperitoneally in the amount of 30 or 60 mg/kg into a uPA-Tg(+/−)/SCID mouse and a uPA-Tg(+/+)/SCID mouse. As the result, number of colonies of normalized hepatocytes caused by deletion of introduced uPA gene (uPA-Tg(−/−)/SCID) was reduced in the uPA-Tg (+/−)/SCID mouse (FIG. 12).

Then, the uPA-Tg(+/−)/SCID and the uPA-Tg(+/+)/SCID mice, which were inoculated with 60 mg/kg of retrorsine intraperitoneally, were transplanted with human hepatocytes similarly as in Example 1 to prepare chimeric mice. As the result, human albumin concentration in the blood of the chimeric uPA-Tg(+/−)/SCID mouse was also increased to the same level as that of the chimeric uPA-Tg(+/+)/SCID mouse.

Example 5

Administration of an Anti-mouse Fas Antibody into a Human Hepatocytes Chimeric Mouse As to one chimeric mouse prepared in Example 1, at 100 days after transplantation of human hepatocytes, an anti-mouse Fas antibody which leads mouse hepatocytes to apoptosis by reaction with a Fas antigen thereof was inoculated (0.2 μg/g body weight) into the abdominal cavity of said chimeric mouse twice at the interval of 1 week.

Figure 13:
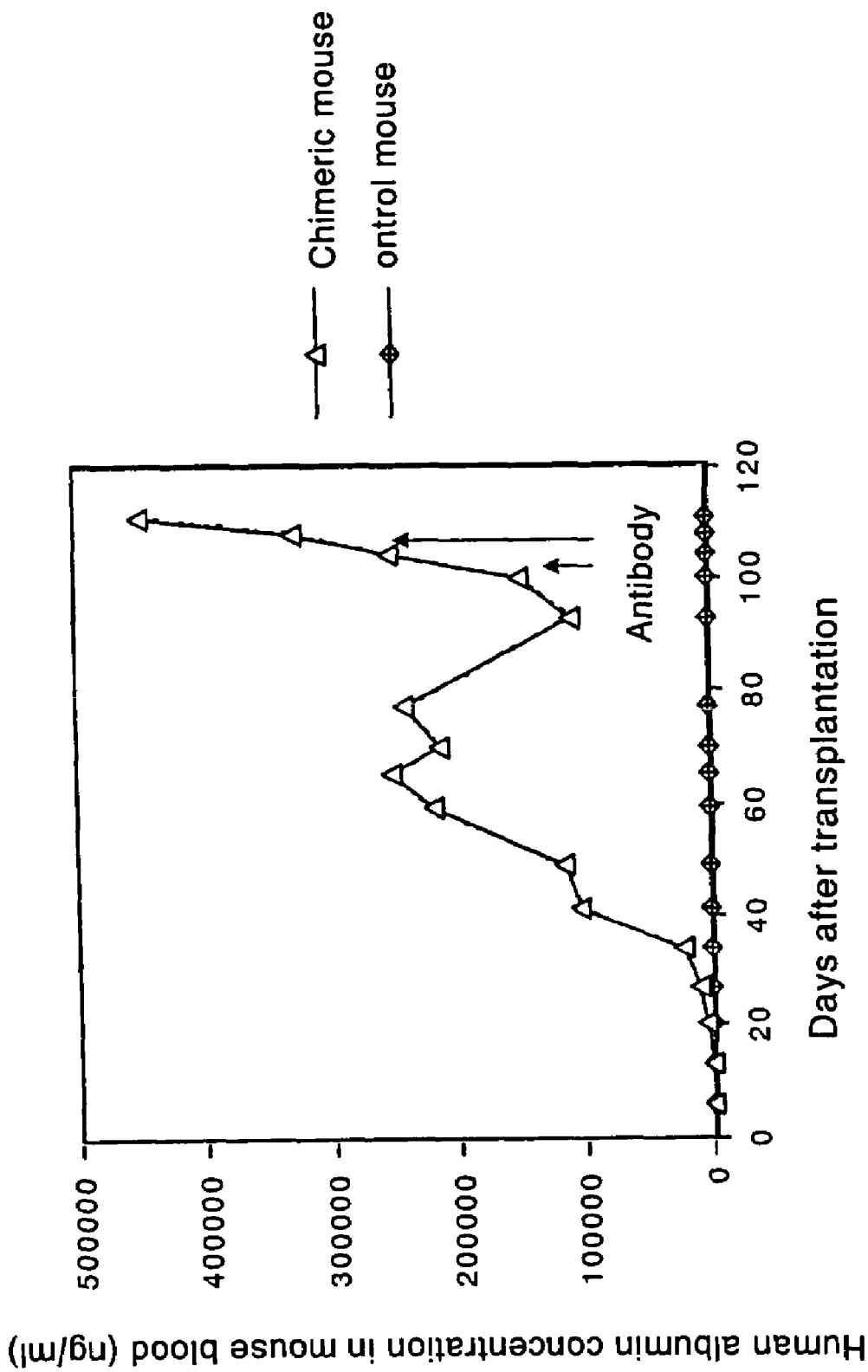
FIG. 13 is test result on human albumin concentration in mice blood administered with an anti-mouse Fas antibody in human hepatocytes chimeric mice.

As the results shown in FIG. 13, in this chimeric mouse, concentration of human albumin in blood thereof indicates a declining tendency after about 80 days from transplantation of human hepatocytes, however, concentration of those was significantly increased by administration of the anti-mouse Fas antibody.

In consequence, in the method of the present invention, it was confirmed that administration of the anti-mouse Fas antibody into a chimeric mouse just after transplantation of human hepatocytes was effective to proliferation and/or activation of human hepatocytes.

Example 6

Figure 14:
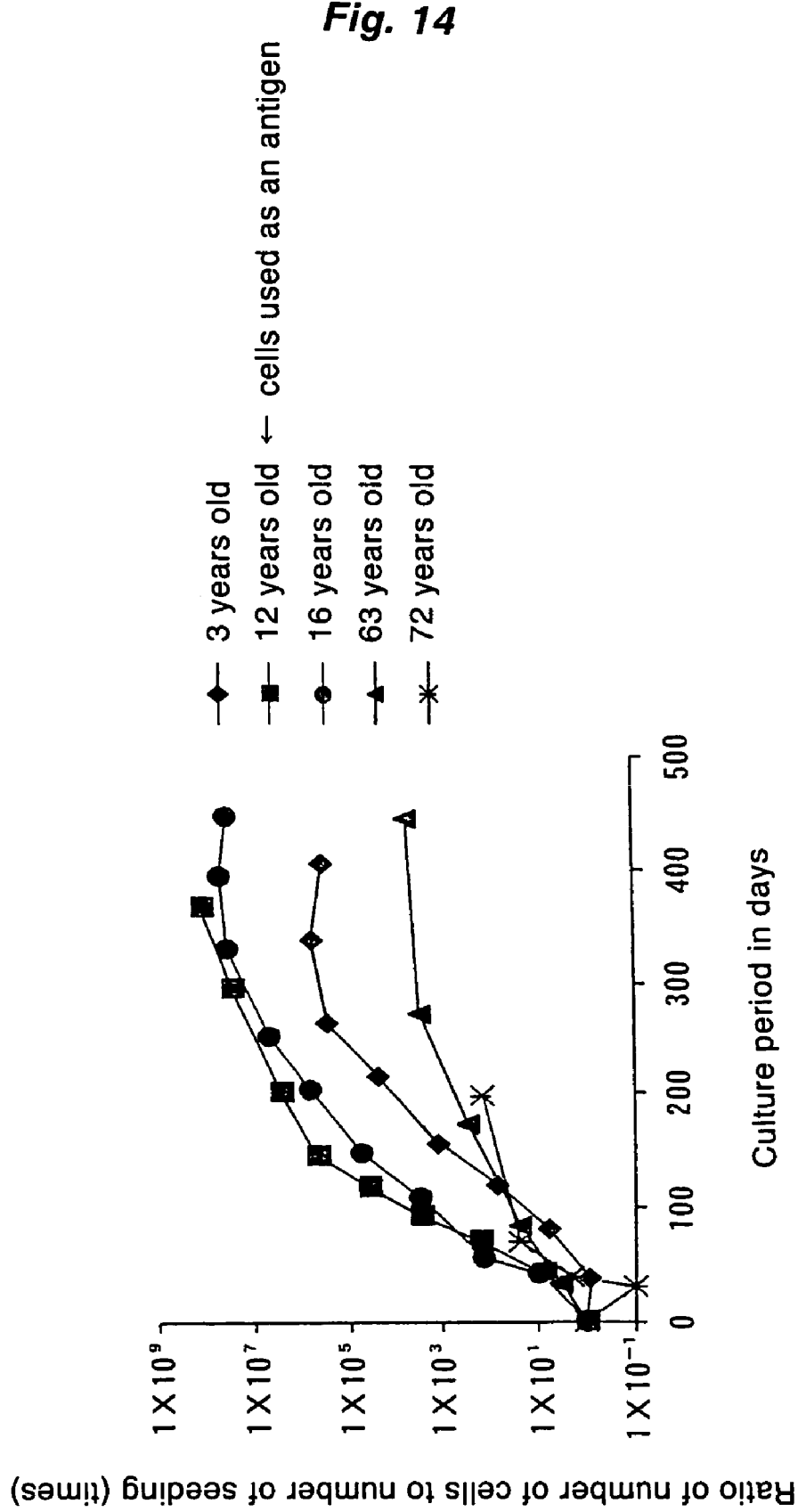
FIG. 14 illustrates a growth curve in culturing hepatocytes collected from patients of various ages.

Preparation of a Monoclonal Antibody Which Specifically Recognizes Human Proliferative Hepatocytes 1. Culture of Human Hepatocytes A dispersed cell suspension was obtained from a human liver tissue by a collagenase perfusion method. The dispersed cell suspension was subjected to low-speed centrifugation (50×g, for 2 minutes), and the sedimentary fraction was co-cultured with mitomycin C-treated Swiss 3T3 cells using Dulbecco's modified Eagle's medium (DMEM) added with fetal calf serum, human serum, EGF, nicotinamide and activity-persistent type vitamin C. Swiss 3T3 cells were added every ten days. Human hepatocytes colonies were observed after about 7 days of culture. Proliferated hepatocytesin confluent were subcultured by using EDTA/Trypsin. Hepatocytes of children could be subcultured up to 6-9 passages, however, hepatocytes of patients, not younger then 60 years old, could only be subcultured until 3-4 passages (FIG. 14). The hepatocytes of the child (12 years old) exhibiting the highest proliferation ability were used as an antigen (FIG. 15).

2. Immunization of Animals

The hepatocytes of the child (12 years old) at 3-5 passages by the above-described method were proliferated on culture dishes. After confluent-proliferated cells (about $1 \times 10^7$ cells) were washed with PBS (a phosphate buffer salt solution), PBS was removed and the cells were scraped with a cell scraper to suspend in about 1 ml PBS. Thus obtained suspension was administered intraperitoneally in Balb/c mice, 6 weeks old. Immunization was further performed by a similar method after 20 days or 30 days.

3. Cell Fusion

After twice immunization, increased antibody titer was observed. After 72 hours of the third immunization (boost), a spleen was extracted from an immunized animal to collect spleen cells. These spleen cells and mouse myeloma cells (cell line name: NS-1) were fused, plated into 372 wells of 96-well plates and cultured.

4. Screening of Hybridoma

Primary Screening (ELISA, Tissue Staining)

Reactivity of culture supernatant of the fused cells thus obtained to an antigen was assayed by ELISA. Assay was performed by the following method. The subcultured hepatocytes used as the antigen were plated on the 96-well plate, followed by washing with PBS after cultivation, drying and storing at −80° C., to which the culture supernatant was reacted. An enzyme labeled anti-mouse IgG antibody or anti-mouse IgM antibody was then reacted thereto, followed by developing color by adding substrate to measure absorbance. As the results, mean absorbance of the 372 fused cell samples was 0.149 (SD: 0.099), and samples with absorbance of not lower than 0.20 (81 samples, about 20%) were defined as positive samples. Since color development was also confirmed in naked eye observation in samples with absorbance of not lower than 0.15, samples with the absorbance of from 0.15 to 0.20 (46 samples) were treated with tissue staining to confirm reactivity. Among them, only 13 samples showing interesting staining pattern were selected as positive samples. Selected 94 positive samples were further cultured in large scale, and culture supernatant was recovered and cells were stored in a frozen state.

5. Secondary Screening (ELISA, Tissue Staining)

From 94 samples selected by the primary screening, 88 positive samples were selected by measuring reactivity against an antigen in culture supernatant after the large scale cultivation, by ELISA similarly as in the primary screening. Reactivity in tissue of these samples was studied by tissue staining. Samples containing hybridoma, which specifically reacts with cell membrane of hepatocytes and hepatocytes in portal region, or culture supernatant of the clone obtained by cloning therefrom, were studied on reactivity against human hepatocytes immediately after separation.

Figure 17:
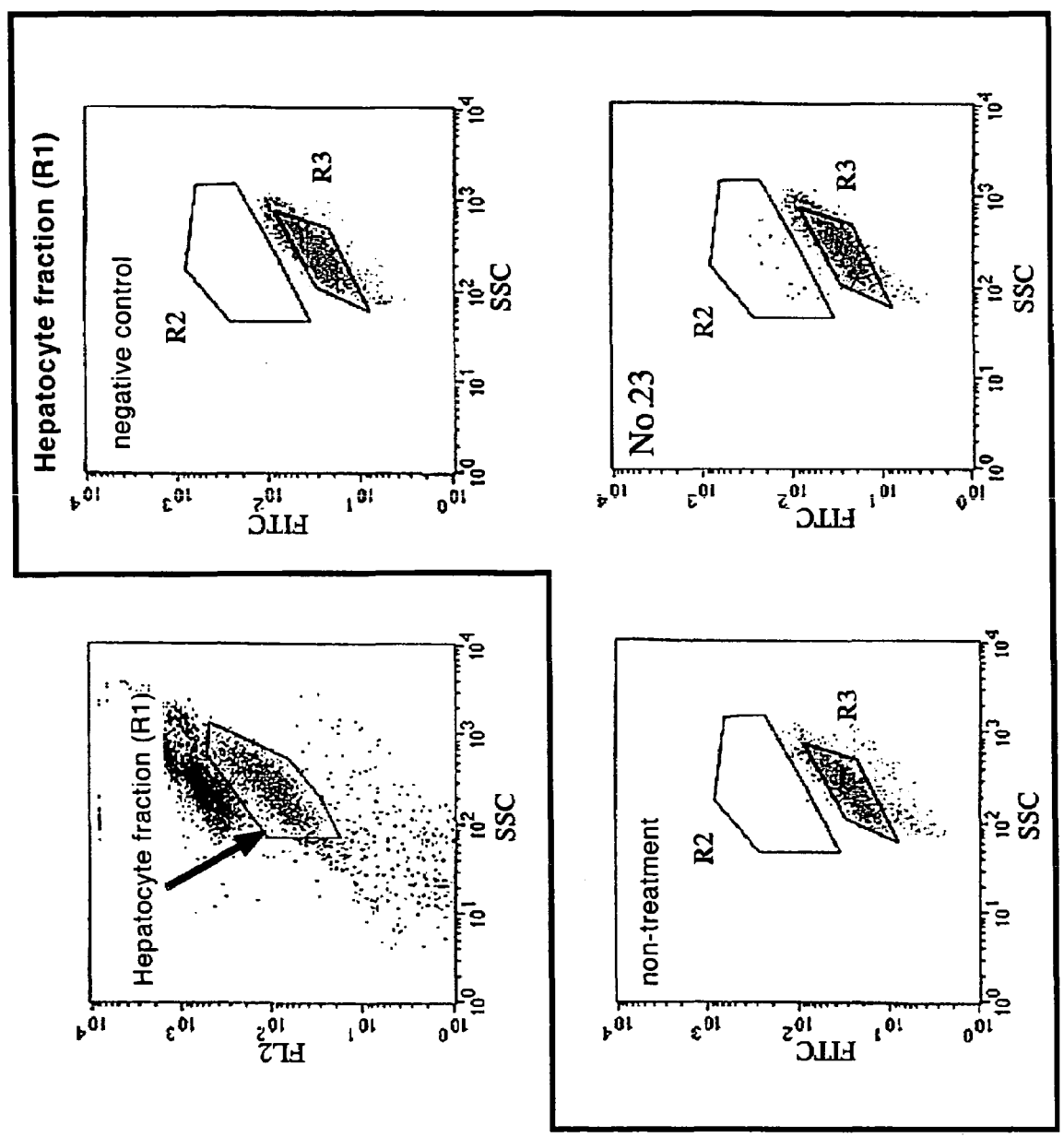
FIG. 17 is a result analyzed by FACS of reactivity of hybridoma (No. 23)culture supernatantat human hepatocytes surface immediately after separation.
Figure 19:
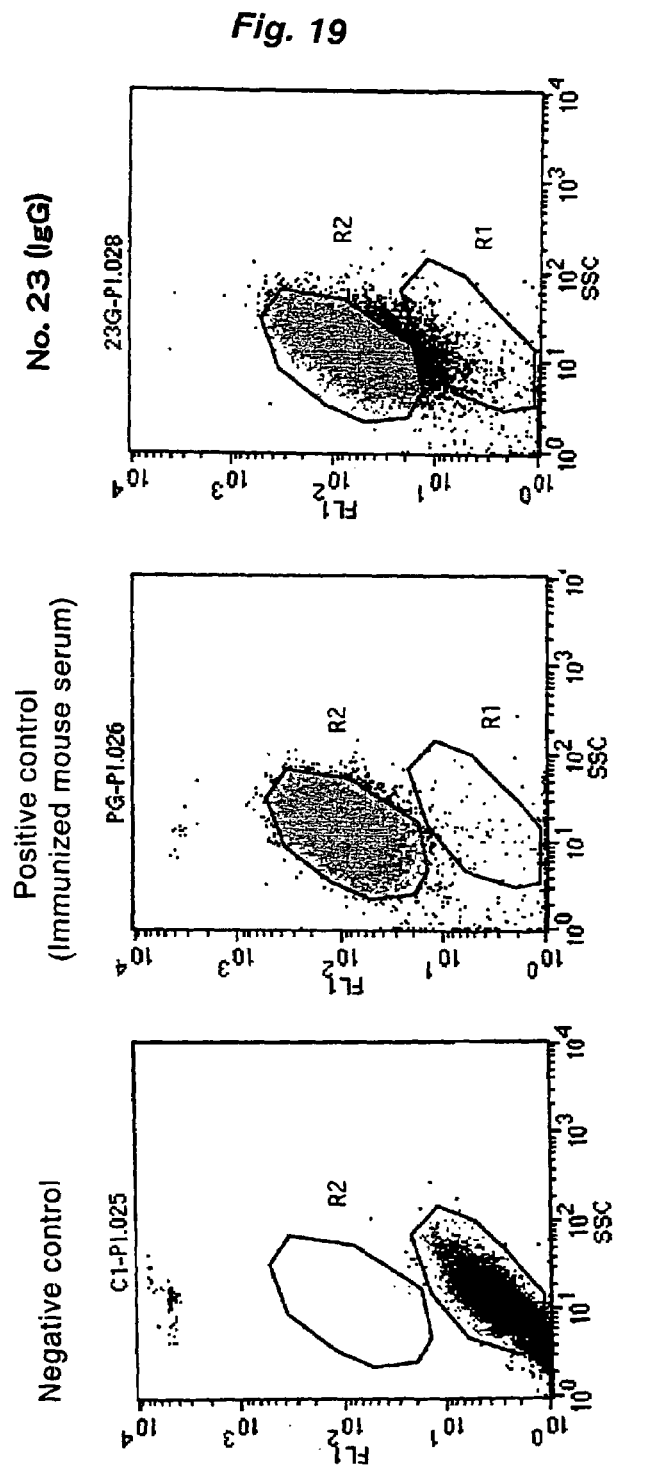
FIG. 19 is a result analyzed by FACS of reactivity of hybridoma (No. 23) culture supernatant at subcultured human hepatocytes surface.

Supernatant No.23 (FIG. 16) of cultured hybridoma, in which the hepatocytes membrane of the portal region was stained in tissue, was analyzed on reactivity at hepatocytes surface immediately after separation, by using FACS (fluorescence activated cell sorting). Hepatocytes of adult men, 46 years old and 49 years old, obtained by collagenase perfusion and low-speed centrifugation, were treated with culture supernatant of this sample at 4° C. for 30 minutes, and an FITC labeled anti-mouse IgG antibody was then treated at 4° C. for 30 minutes to make detection by FACS possible. As the result, a part of cells (1- 2%) in a hepatocyte population reacted with the sample (FIG. 17). The reacted cell population, designated as R2 fraction, and the non-reacted cell population, designated as R3 fraction, were fractionated and cultured. Hepatocytes before fractionation were also cultured. As the result, colony formation was observed on culture after about 7 days in the hepatocytes before fractionation as described hereinbefore. On the other hand, colony-forming cells were not observed in the R3 fraction, but large numbers of colony were observed in the R2 fraction reacted with No.23 (FIG. 18). Reactivity with the subcultured human hepatocytes was examined by FACS, and about 80% of the cells were found to be positive (FIG. 19). Namely, it was considered that among the subcultured human hepatocytes, the differentiated cells during culturing process were not recognized and only the proliferative hepatocytes were recognized. From these results, No.23 was suggested to contain hybridoma which specifically recognized colony-forming cells. Clones obtained by cloning from the No.23 sample were analyzed by using FACS on reactivity at hepatocytes surface immediately after separation. As the result, 3 clones showing similar reactivity were obtained. Among these clones, 1 clone (Mouse-Mouse hybridoma K8223) was deposited in The International Patent Organism Depositary, National Institute of Advanced Industrial Science and Technology (Deposition No. FERM P-I8752) on Mar. 6,2002, and was subjected to international deposition on Mar. 20, 2003 (Deposition No. FERM BP-8334).

6. Preparation of a Monoclonal Antibody

The above hybridoma cell (K8223 strain) was cultured, followed by intraperitoneal injection in mice and collection of a monoclonal antibody from ascites to obtain the monoclonal antibody which specifically binds to proliferative human hepatocytes.

Example 7

Figure 20:
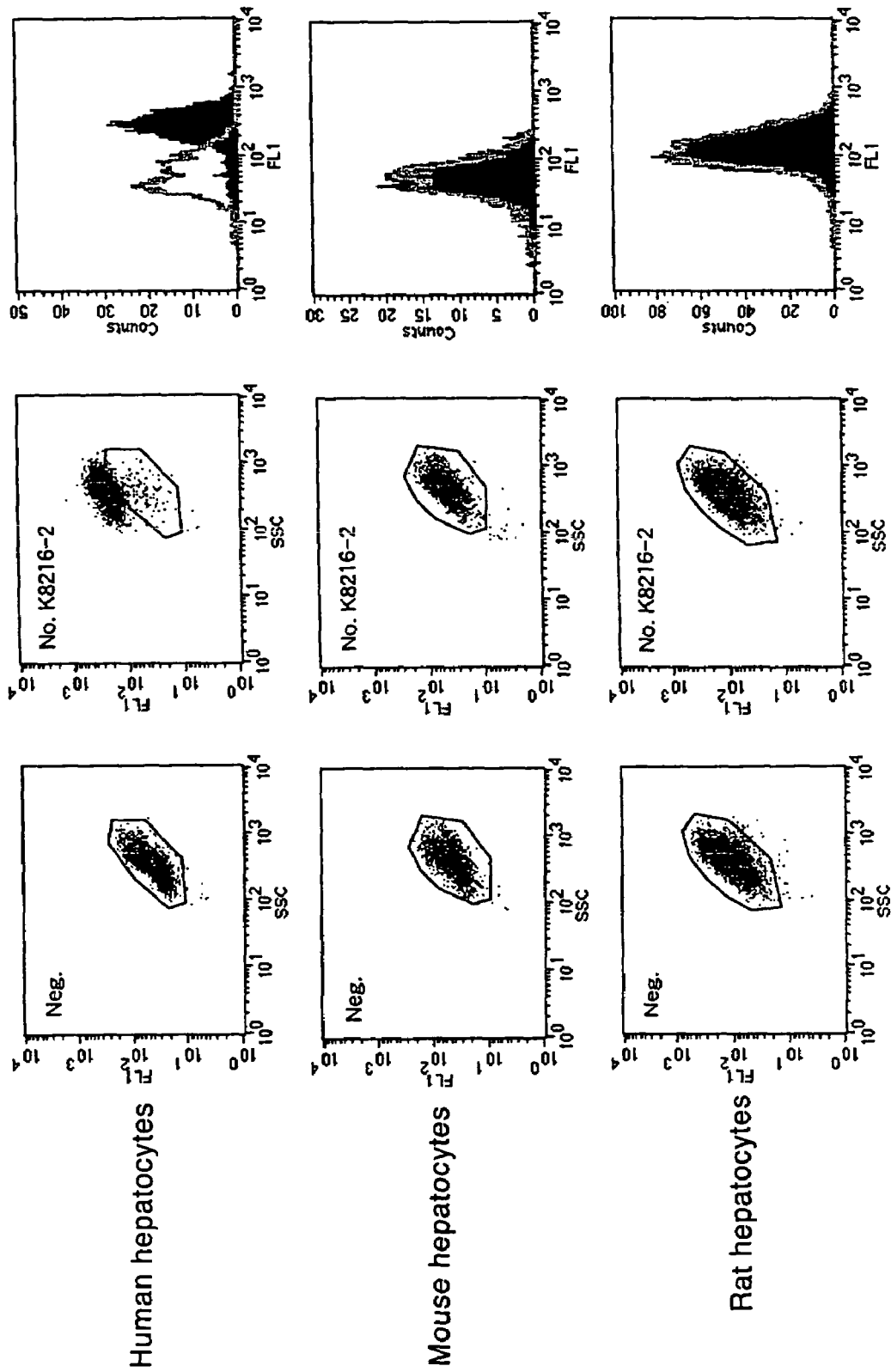
FIG. 20 is a result analyzed by FACS of reactivity of hybridoma (K8216) culture supernatant at human, mouse and rat hepatocytes surfaces immediately after isolation.

Preparation of a Monoclonal Antibody which Specifically Recognizes Human Hepatocytes A hybridoma producing a monoclonal antibody, which specifically recognizes human hepatocytes but does not recognize non-human hepatocytes, was selected from 88 ELISA-positive samples among 94 samples selected at the 1st screening of Example 6 by means of histological staining of a human liver tissue. As to 3 samples of culture supernatant of hybridoma which stained cell membrane of hepatocytes equally irrespective of the hepatic zones, reactivity to cell surface of cultured human hepatocytes, human hepatocytes just after separation and hepatocytes of non-human animals (such as mouse and rat) just after separation was analyzed using FACS. The hepatocytes obtained from a liver of adult men (46 or 68 years old) by collagenase perfusion and low-speed centrifugation were treated with the culture supernatant of the above selected 3 samples at 4° C. for 30 minutes, and then treated with an FITC-labeled anti-mouse IgG antibody at 4° C. for 30 minutes to make detection by FACS possible. As the result of screening by FACS, 1 sample of hybridoma (pre-cloning) which was reactive with only human hepatocytes and not reactive with hepatocytes of mouse and rat was selected. In 2 clones of a monoclonal hybridoma obtained from the above selected hybridoma, each culture supernatant showed similar reactivity (FIG. 20). In histological staining of the culture supernatant of the above selected hybridoma, the region considered to be a bile canaliculi of a human liver tissue was stained, but no zone-specificity in terms of staining properties was confirmed. By the way, the liver tissues of a mouse and a rat were both negative on reactivity with the culture supernatant of the hybridoma. In consequence, the hybridoma that produces an anti-human hepatocytes monoclonal antibody, which specifically recognizes human hepatocytes and does not recognize non-human hepatocytes, was obtained. This hybridoma K8216 strain was deposited to The Patent Creature Deposition Center of The National Institute of Advanced Industrial Science and Technology in Japan as of Mar. 6, 2002 (deposition number: FERM P-18751), and also deposited to The International Depository Center as of Mar. 20, 2003 (deposition number: FERM BP-8333).

A monoclonal antibody was obtained from the K8216 strain by similar procedures as described in Example 6.

INDUSTRIAL APPLICABILITY

By the present invention, as described above in detail, proliferation of human hepatocytes in large scale with keeping its original function can be attained. Furthermore, a chimeric mouse in which many cells in the liver are replaced with human hepatocytes is provided. Drug metabolism tests and safety tests of compounds can be available by the use of said chimeric mouse or human hepatocytes.

The invention claimed is:

1. A method for proliferating human hepatocytes, which comprises transplanting proliferative human hepatocytes into the liver of an immunodeficient hepatopathy mouse, administering to the mouse an effective amount of a complement inhibitor to protect against tissue damage associated with human complement produced by the human hepatocytes, and proliferating said human hepatocytes in the liver of said mouse.

2. The method for proliferating human hepatocytes of claim 1, wherein the proliferative human hepatocytes are human hepatocytes recognized by a monoclonal antibody which specifically recognizes human hepatocytes which proliferate to form a colony.

3. The method for proliferating the human hepatocytes of claim 2, wherein the monoclonal antibody is one produced from Mouse-Mouse hybridoma K8223 (FERM BP-8334).

4. A method for large scale proliferation of human hepatocytes, which comprises the following steps (1) to (3), and the steps (2) and (3) are repeated at least once;
   (1) a step comprising transplanting proliferative human hepatocytes into the liver of an immunodeficient hepatopathy mouse, and then proliferating the transplanted human hepatocytes in the mouse liver;
   (2) a step of isolating the proliferated human hepatocytes from the mouse liver; and
   (3) a step comprising transplanting the human hepatocytes isolated from the mouse liver into the liver of an immunodeficient hepatopathy mouse, and then proliferating the human hepatocytes in the liver of said mouse for not shorter than 50 days, wherein each of the mice transplanted with the human hepatocytes in step (1) and step (3) is administered an effective amount of a complement inhibitor to protect against tissue damage associated with human complement produced by the human hepatocytes.

5. The method for large scale proliferation of human hepatocytes of claim 4, wherein the proliferative human hepatocytes are human hepatocytes recognized by a monoclonal antibody which specifically recognizes human hepatocytes which proliferate to form a colony.

6. The method for large scale proliferation of human hepatocytes of claim 5, wherein the monoclonal antibody is one produced from Mouse-Mouse hybridoma K8223 (FERM BP-8334).

* * * * *